US 12,268,735 B2
United States Patent
Weiner et al.

(10) Patent No.: US 12,268,735 B2
(45) Date of Patent: *Apr. 8, 2025

(54) *Marburgvirus* CONSENSUS ANTIGENS, NUCLEIC ACID CONSTRUCTS AND VACCINES MADE THEREFROM, AND METHODS OF USING SAME

(71) Applicants: The Trustees of the University of Pennsylvania, Philadelphia, PA (US); The Wistar Institute of Anatomy and Biology, Philadelphia, PA (US)

(72) Inventors: David Weiner, Merion, PA (US); Ami Patel, Philadelphia, PA (US); Sarah Elliott, Pullman, WA (US)

(73) Assignees: The Wistar Institute of Anatomy and Biology, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/179,668

(22) Filed: Mar. 7, 2023

(65) Prior Publication Data
US 2023/0293664 A1    Sep. 21, 2023

Related U.S. Application Data

(63) Continuation of application No. 16/465,691, filed as application No. PCT/US2017/064135 on Dec. 1, 2017, now Pat. No. 11,596,678.

(60) Provisional application No. 62/429,473, filed on Dec. 2, 2016.

(51) Int. Cl.
| | | |
|---|---|---|
| *A61K 39/12* | (2006.01) | |
| *A61P 31/14* | (2006.01) | |
| *A61P 37/04* | (2006.01) | |
| *C07K 14/005* | (2006.01) | |
| *A61K 39/00* | (2006.01) | |

(52) U.S. Cl.
CPC .............. *A61K 39/12* (2013.01); *A61P 31/14* (2018.01); *A61P 37/04* (2018.01); *C07K 14/005* (2013.01); *A61K 2039/53* (2013.01); *C12N 2760/14222* (2013.01); *C12N 2760/14234* (2013.01)

(58) Field of Classification Search
None
See application file for complete search history.

(56) References Cited

U.S. PATENT DOCUMENTS

| | | | | |
|---|---|---|---|---|
| 7,731,975 | B2 * | 6/2010 | Grogan | C07K 14/005 |
| | | | | 435/320.1 |
| 9,597,388 | B2 | 3/2017 | Weiner | |
| 10,034,930 | B2 | 7/2018 | Weiner | |
| 10,765,733 | B2 | 9/2020 | Weiner | |
| 11,596,678 | B2 * | 3/2023 | Weiner | C07K 14/005 |
| 2003/0108560 | A1 | 6/2003 | Grogan | |
| 2007/0041941 | A1 | 2/2007 | Weiner | |
| 2011/0104105 | A1 | 5/2011 | Weiner | |
| 2015/0335726 | A1 * | 11/2015 | Weiner | C07K 14/005 |
| | | | | 424/186.1 |
| 2017/0165350 | A1 | 6/2017 | Weiner | |

FOREIGN PATENT DOCUMENTS

WO    2016097065 A1    6/2016

OTHER PUBLICATIONS

Towner et al. (Journal of Virology, 2006, p. 6497-6516) in Towner et al. (Journal of Virology, 2006, p. 6497-6516) Towner et al. (Journal of Virology, 2006, p. 6497-6516) in parent U.S. Appl. No. 16/465,691.*
"UniProtKB-P35253—Envelope glycoprotein precursor—Lake Victoria marburgvirus (strain Musoke-80) (MARV)—GP gene & protein", Jan. 25, 2016, XP055244338, Retrieved from the Internet: URL: http://www.uniprot.org/uniprot/P35253, 1 page.
Bagarazzi ML et al., "Immunotherapy Against HPV16/18 Generates Potent TH1 and Cytotoxic Cellular Immune Responses", Sci. Transl. Med., 2011, 4:155ra138, 33 pages.
Blaney JE et al., "Live attenuated recombinant vaccine protects nonhuman primates against Ebola and Marburg viruses", Nat. Med., 2005, 11:786-790.
Bradfute SB et al., "Filovirus vaccines", Hum. Vaccin., 2011, 7:701-711.
Falzarano D et al., "Progress in filovirus vaccine development: evaluating the potential for clinical use", Expert Rev. Vaccines, 2011, 10:63-77.
Feldmann H et al., "Ebola virus: from discovery to vaccine", Nat. Rev. Immunol., 2003, 3:677-685.
Geisbert et al., "Single-Injection Vaccine Protects Nonhuman Primates against Infection with Marburg Virus and Three Species of Ebola Virus," Journal of Virology, 2009, 83:7296-7304.
Geisbert TW et al., "Vector choice determines immunogenicity and potency of genetic vaccines against Angola Marburg virus in nonhuman primates", J. Virol., 2010, 84:10386-10394.

(Continued)

*Primary Examiner* — Agnieszka Boesen
(74) *Attorney, Agent, or Firm* — Riverside Law LLP

(57)    ABSTRACT

Nucleic acid molecules and compositions comprising one or more nucleic acid sequences that encode a consensus Marburgvirus filovirus glycoprotein immunogens. Immunomodulatory methods and methods of inducing an immune response against Marburgvirus are disclosed. Method of preventing infection by Marburgvirus and methods of treating individuals infected with Marburgvirus are disclosed. Consensus Marburgvirus filovirus glycoprotein immunogens are disclosed.

20 Claims, 10 Drawing Sheets
Specification includes a Sequence Listing.

(56) References Cited

OTHER PUBLICATIONS

Geisbert, T et al., 'Recombinant Vesicular Stomatitis Virus-Based Vaccines Against Ebola and Marburg Virus Infections.', JID., (2011), vol. 204, No. SUPPL, pp. S1075-S1081, XP002688258.

Grant-Klein RJ et al., "A multiagent filovirus DNA vaccine delivered by intramuscular electroporation protects mice from ebola and Marburg virus challenge", Hum. Vaccin. Immunother., 2012, 8:1703-1706.

He et al., "Emerging Vaccine Informatics", J Biomed Biotechnol 2010:1-26.

Hirao LA et al., "Multivalent smallpox DNA vaccine delivered by intradermal electroporation drives protective immunity in nonhuman primates against lethal monkeypox challenge", J. Infect. Dis., 2011, 203:95-102.

Kalina WV et al., "Discovery of common marburgvirus protective epitopes in a BALB/c mouse model", Virol. J., 2009, 6:132.

Kobinger GP et al., "Replication, pathogenicity, shedding, and transmission of Zaire ebolavirus in pigs", J. Infect. Dis., 2011, 204:200-208.

Mire et al., "Durability of a Vesicular Stomatitis Virus-Based Marburg Virus Vaccine in Nonhuman Primates," PLoS One, 2014, 9:e94355, 7 pages.

Outbreak news, "Ebola Reston in pigs and humans, Philippines", Wkly Epidemiol Rec., 2009, 84:49-50.

Riemenschneider et al., "Comparison of individual and combination DNA vaccines for B. anthracis, Ebola virus, Marburg virus and Venezuelan equine encephalitis virus," 2003, Vaccine 21: 4071-4080.

Sardesai et al., "Electroporation Delivery of DNA Vaccines: Prospects for Success", Curr. Opin. Immunol., 2011, 23:421-429.

Swenson et al., "Virus-like particles exhibit potential as a pan-filovirus vaccine for both Ebola and Marburg viral infections," 2005, Vaccine 23: 3033-3042.

Towner et al. (Journal of Virology, 2006, p. 6497-6516).

Towner JS et al., "Marburgvirus genomics and association with a large hemorrhagic fever outbreak in Angola", J. Virol., 2006, 80:6497-6516.

Warfield KL et al., "Protective role of cytotoxic T lymphocytes in filovirus hemorrhagic fever", J. Biomed. Biotechnol., 2011:984241, 14 pages.

\* cited by examiner

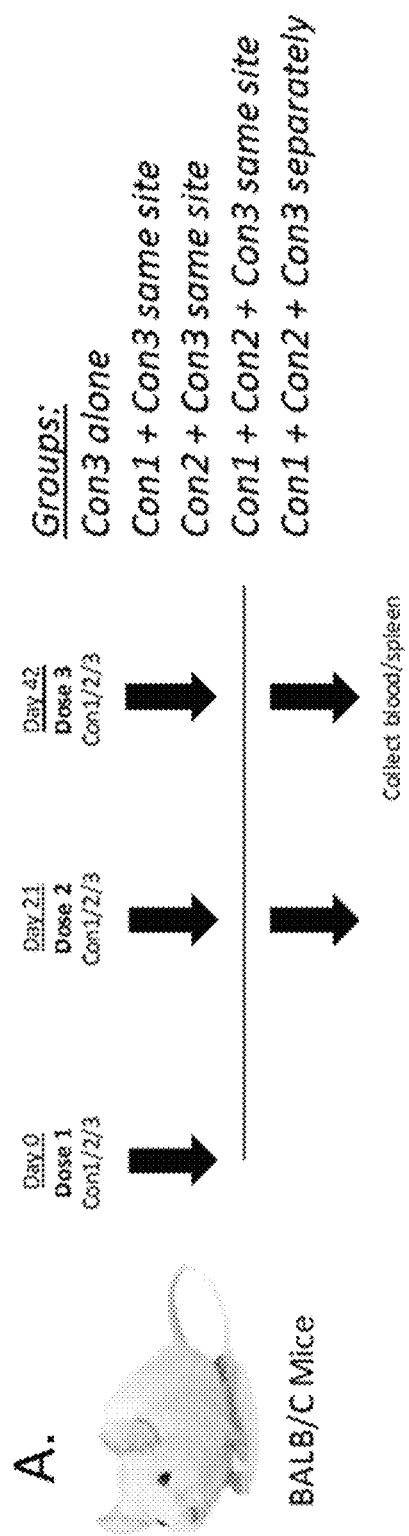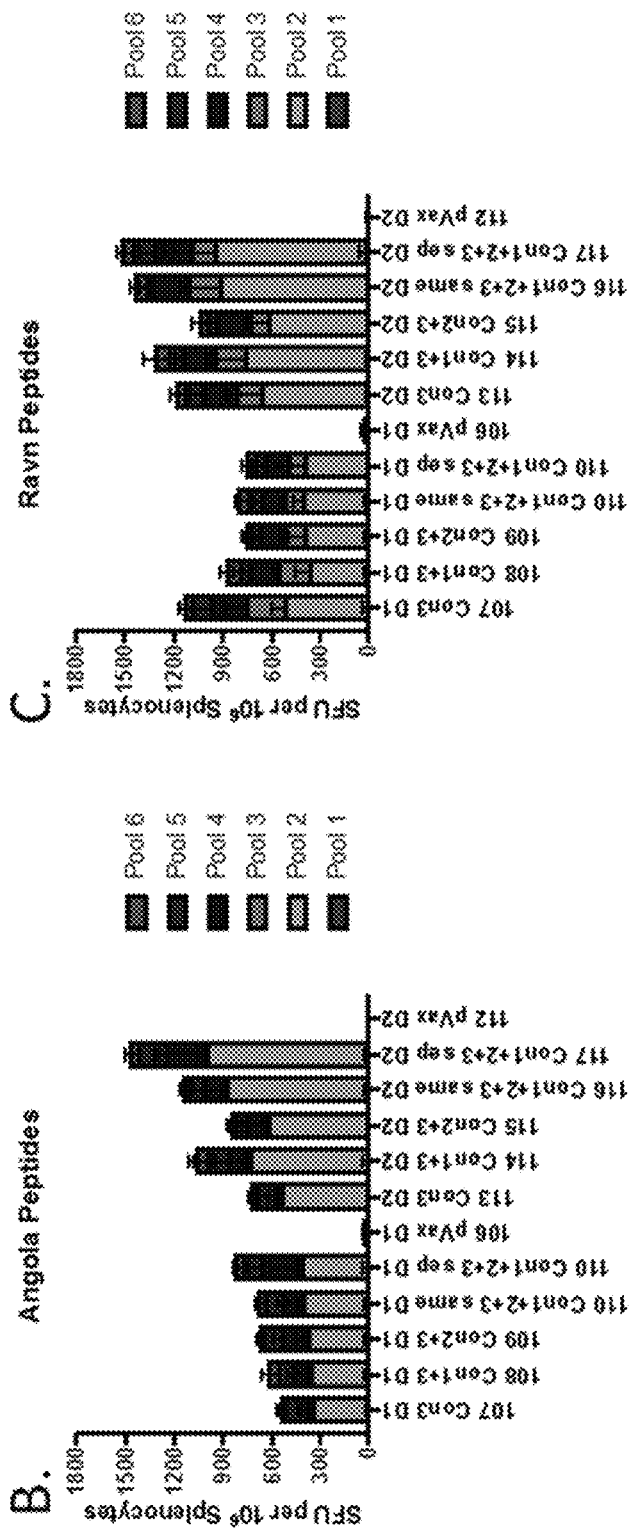
Figure 7A – 7C

Marburgvirus CONSENSUS ANTIGENS, NUCLEIC ACID CONSTRUCTS AND VACCINES MADE THEREFROM, AND METHODS OF USING SAME

CROSS-REFERENCE TO RELATED APPLICATIONS

This application is a Continuation of U.S. national phase application Ser. No. 16/465,691, filed May 31, 2019, filed under 35 U.S.C. § 371 claiming priority to International Patent Application No. PCT/US17/64135, filed Dec. 1, 2017, which is entitled to priority under 35 U.S.C. § 119 (e) to U.S. Provisional Patent Application No. 62/429,473, filed Dec. 2, 2016, the contents of each of which are incorporated by reference herein in their entireties.

REFERENCE TO A "SEQUENCE LISTING," A TABLE, OR A COMPUTER PROGRAM LISTING APPENDIX SUBMITTED AS AN XML FILE

The Sequence Listing written in the XML text file: "206193-0025-01US_SequenceListing"; created on Mar. 7, 2023, and 19,696 bytes in size, is hereby incorporated by reference.

FIELD OF THE INVENTION

The present invention relates to vaccines for inducing immune responses and preventing Marburgvirus infection and/or treating individuals infected with Marburgvirus. The present invention relates to consensus Marburgvirus proteins and nucleic acid molecules which encode the same.

BACKGROUND OF THE INVENTION

The Filoviridae are non-segmented, single stranded RNA viruses which contain two divergent genera, Marburgvirus (MARV) and Ebolavirus (EBOV). Members from each can cause severe and highly lethal hemorrhagic fever disease to which there is no cure or licensed vaccine (Bradfute S. B., et al. (2011) Filovirus vaccines. Hum Vaccin 7:701-711; Falzarano D., et al. (2011) Progress in filovirus vaccine development: evaluating the potential for clinical use. Expert Rev Vaccines 10:63-77; and Towner J. S., et al. (2006) Marburgvirus genomics and association with a large hemorrhagic fever outbreak in Angola. J Virol 80:6497-6516).

The haemorrhagic fever diseases are acute infectious with no carrier state, although they are easily transmissible among humans and nonhuman primates by direct contact with contaminated bodily fluids, blood, and tissue (Feldmann H., et al. (2003) Ebola virus: from discovery to vaccine. Nat Rev Immunol 3:677-685). During outbreak situations, reuse of medical equipment, health care facilities with limited resources, and untimely application of prevention measures escalate transmission of the disease, allowing amplification of infections in medical settings.

Since the natural reservoirs of these zoonotic pathogens are likely to be African bats and pigs (Kobinger G. P., et al. (2011) Replication, pathogenicity, shedding, and transmission of Zaire ebolavirus in pigs. J Infect Dis 204:200-208), the latter possibly being more of an amplifying host, the manner in which the virus first appears at the start of an outbreak is thought to occur through human contact with an infected animal. Unpredictable endemic surfacing in the Philippines, potentially Europe, and primarily Africa of this disease further constitutes a major public health concern (Outbreak news. (2009) Ebola Reston in pigs and humans, Philippines. Wkly Epidemiol Rec 84:49-50).

Vaccine-induced adaptive immune responses have been described in numerous preclinical animal models (Blaney J E, et al. (2011). Live attenuated recombinant vaccine protects nonhuman primates against Ebola and Marburg viruses. Nat Med 11:786-790; Kalina W V, Warfield K L, Olinger G G, Bavari S (2009). Discovery of common marburgvirus protective epitopes in a BALB/c mouse model. Virol J 6:132; Grant-Klein R J et al. (2012) A multiagent filovirus DNA vaccine delivered by intramuscular electroporation protects mice from ebola and Marburg virus challenge. Hum Vaccin Immunother 8; 1703-6; Geisbert T W et al. (2010) Vector choice determines immunogenicity and potency of genetic vaccines against Angola Marburg virus in nonhuman primates. J Virol 84:10386-10394.) Viral vaccines have shown promise and include mainly the recombinant adenoviruses and vesicular stomatitis viruses. Non-infectious strategies such as recombinant DNA and Antigen-coupled virus-like particle (VLP) vaccines have also demonstrated levels of preclinical efficacy and are generally considered to be safer than virus-based platforms. (Warfield K L, Olinger G G (2011) Protective role of cytotoxic T lymphocytes in filovirus hemorrhagic fever. J Biomed Biotechnol 2011:984241). T cells have also been shown to provide protection based on studies performed in knockout mice, depletion studies in NHPs, and murine adoptive transfer studies where efficacy was greatly associated with the lytic function of adoptively-transferred CD8+ T cells. However, little detailed analysis of this response as driven by a protective vaccine has been reported.

Therefore, there is need in the art for protective vaccines against Marburgvirus. The current invention satisfies this unmet need.

SUMMARY OF THE INVENTION

A composition comprising a nucleic acid sequence that encodes a synthetic consensus Marburg marburgvirus envelope glycoprotein immunogen is provided. The amino acid sequence of the synthetic consensus Marburg marburgvirus envelope glycoprotein immunogen may be SEQ ID NO:2, SEQ ID NO:4 or SEQ ID NO:6, a fragment of SEQ ID NO: 2, SEQ ID NO:4 or SEQ ID NO:6, an amino acid sequence that is homologous to SEQ ID NO: 2, SEQ ID NO:4 or SEQ ID NO:6, or a fragment of an amino acid sequence that is homologous to SEQ ID NO:2, SEQ ID NO:4 or SEQ ID NO:6. Amino acid sequences that are homologous to SEQ ID NO:2, SEQ ID NO:4 or SEQ ID NO:6 are typically 95% or more, 96% or more, 97% or more, 99% or more, or 99% or more, homologous to SEQ ID NO:2, SEQ ID NO:4 or SEQ ID NO:6. Fragments of SEQ ID NO:2, SEQ ID NO:4 or SEQ ID NO: 6 or fragments of amino acid sequences that are homologous to SEQ ID NO:2, SEQ ID NO: 4 or SEQ ID NO:6 are typically 600 or more, 637 or more, or 670 or more amino acids. The amino acid sequence may optionally comprise a leader sequence, e.g. the IgE signal peptide having an amino acid sequence as set forth in SEQ ID NO:8.

A composition comprising a nucleic acid sequence that encodes a Marburg marburgvirus first consensus envelope glycoprotein immunogen, a nucleic acid sequence that encodes a Marburg marburgvirus second consensus envelope glycoprotein immunogen, and a nucleic acid sequence that encodes a Marburg marburgvirus third consensus envelope glycoprotein immunogen is also provided. The amino acid sequence of the Marburg marburgvirus first consensus envelope glycoprotein immunogen may be SEQ ID NO:2, a fragment of SEQ ID NO:2, an amino acid sequence that is homologous to SEQ ID NO:2, or a fragment of an amino acid sequence that is homologous to SEQ ID NO:2. Amino acid sequences that are homologous to SEQ ID NO:2 are typically 95% or more, 96% or more, 97% or more, 99% or more, or 99% or more, homologous to SEQ ID NO:2. Fragments of SEQ ID NO:2 or fragments of amino acid sequences that are homologous to SEQ ID NO:2 are typically 600 or more, 637 or more, or 670 or more amino acids. The amino acid sequence of the Marburg marburgvirus second consensus envelope glycoprotein immunogen may be SEQ ID NO:4, a fragment of SEQ ID NO:4, an amino acid sequence that is homologous to SEQ ID NO:4, or a fragment of an amino acid sequence that is homologous to SEQ ID NO:4. Amino acid sequences that are homologous to SEQ ID NO:4 are typically 95% or more, 96% or more, 97% or more, 99% or more, or 99% or more, homologous to SEQ ID NO:4. Fragments of SEQ ID NO:4 or fragments of amino acid sequences that are homologous to SEQ ID NO:4 are typically 600 or more, 637 or more, or 670 or more amino acids. The amino acid sequence of the Marburg marburgvirus third consensus envelope glycoprotein immunogen may be SEQ ID NO:6, a fragment of SEQ ID NO:6, an amino acid sequence that is homologous to SEQ ID NO:6, or a fragment of an amino acid sequence that is homologous to SEQ ID NO:6. Amino acid sequences that are homologous to SEQ ID NO: 6 are typically 95% or more, 96% or more, 97% or more, 99% or more, or 99% or more, homologous to SEQ ID NO:6. Fragments of SEQ ID NO:6 or fragments of amino acid sequences that are homologous to SEQ ID NO:6 are typically 600 or more, 637 or more, or 670 or more amino acids. The amino acid sequence may optionally comprise a leader sequence, e.g. the IgE signal peptide having an amino acid sequence as set forth in SEQ ID NO: 8.

Also provided is a composition comprising a nucleic acid sequence that encodes a consensus Marburg marburgvirus envelope glycoprotein immunogen. The amino acid sequence of the consensus Marburg marburgvirus envelope glycoprotein immunogen may be SEQ ID NO:2, SEQ ID NO:4, or SEQ ID NO:6, a fragment of SEQ ID NO:2, SEQ ID NO: 4, or SEQ ID NO:6, an amino acid sequence that is homologous to SEQ ID NO:2, SEQ ID NO:4, or SEQ ID NO:6, or a fragment of an amino acid sequence that is homologous to SEQ ID NO:2, SEQ ID NO:4, or SEQ ID NO:6. Amino acid sequences that are homologous to SEQ ID NO:2, SEQ ID NO:4, or SEQ ID NO:6 are typically 95% or more, 96% or more, 97% or more, 99% or more, or 99% or more, homologous to SEQ ID NO:2, SEQ ID NO:4, or SEQ ID NO:6. Fragments of SEQ ID NO:2, SEQ ID NO:4, or SEQ ID NO: 6 or fragments of amino acid sequences that are homologous to SEQ ID NO:2, SEQ ID NO: 4, or SEQ ID NO:6 are typically 600 or more, 630 or more, or 660 or more amino acids.

The nucleic acid sequence encoding the consensus Marburg marburgvirus envelope glycoprotein immunogen may be SEQ ID NO:1, SEQ ID NO:3, or SEQ ID NO:5, a fragment of SEQ ID NO:1, SEQ ID NO:3, or SEQ ID NO:5, an amino acid sequence that is homologous to SEQ ID NO:1, SEQ ID NO:3, or SEQ ID NO:5, or a fragment of an amino acid sequence that is homologous to SEQ ID NO:1, SEQ ID NO:3, or SEQ ID NO:5. Amino acid sequences that are homologous to SEQ ID NO:1, SEQ ID NO:3, or SEQ ID NO:5 are typically 95% or more, 96% or more, 97% or more, 99% or more, or 99% or more, homologous to SEQ ID NO:1, SEQ ID NO:3, or SEQ ID NO:5. Fragments of SEQ ID NO:1, SEQ ID NO:3, or SEQ ID NO:5 or fragments of amino acid sequences that are homologous to SEQ ID NO:1, SEQ ID NO:3, or SEQ ID NO:5 are typically 1800 or more, 1890 or more, or 1980 or more nucleotides.

Each of the different nucleic acid sequences may be on a single nucleic acid molecule, may each be on a separate nucleic acid molecules or various permutations. Nucleic acid molecules may be plasmids.

The composition may be formulated for delivery to an individual using electroporation.

The composition may further comprise nucleic acid sequences that encode one or more proteins selected from the group consisting of: IL-12, IL-15 and IL-28.

The composition may be used in methods of inducing an immune response against Marburgvirus.

Methods of treating an individual who has been diagnosed with Marburgvirus comprising administering a therapeutically effective amount of the composition to an individual are provided.

Method of preventing Marburgvirus infection in an individual are provided. The methods comprise administering a prophylactically effective amount of the composition to an individual.

BRIEF DESCRIPTION OF THE DRAWINGS

Figures 1A, 1B:
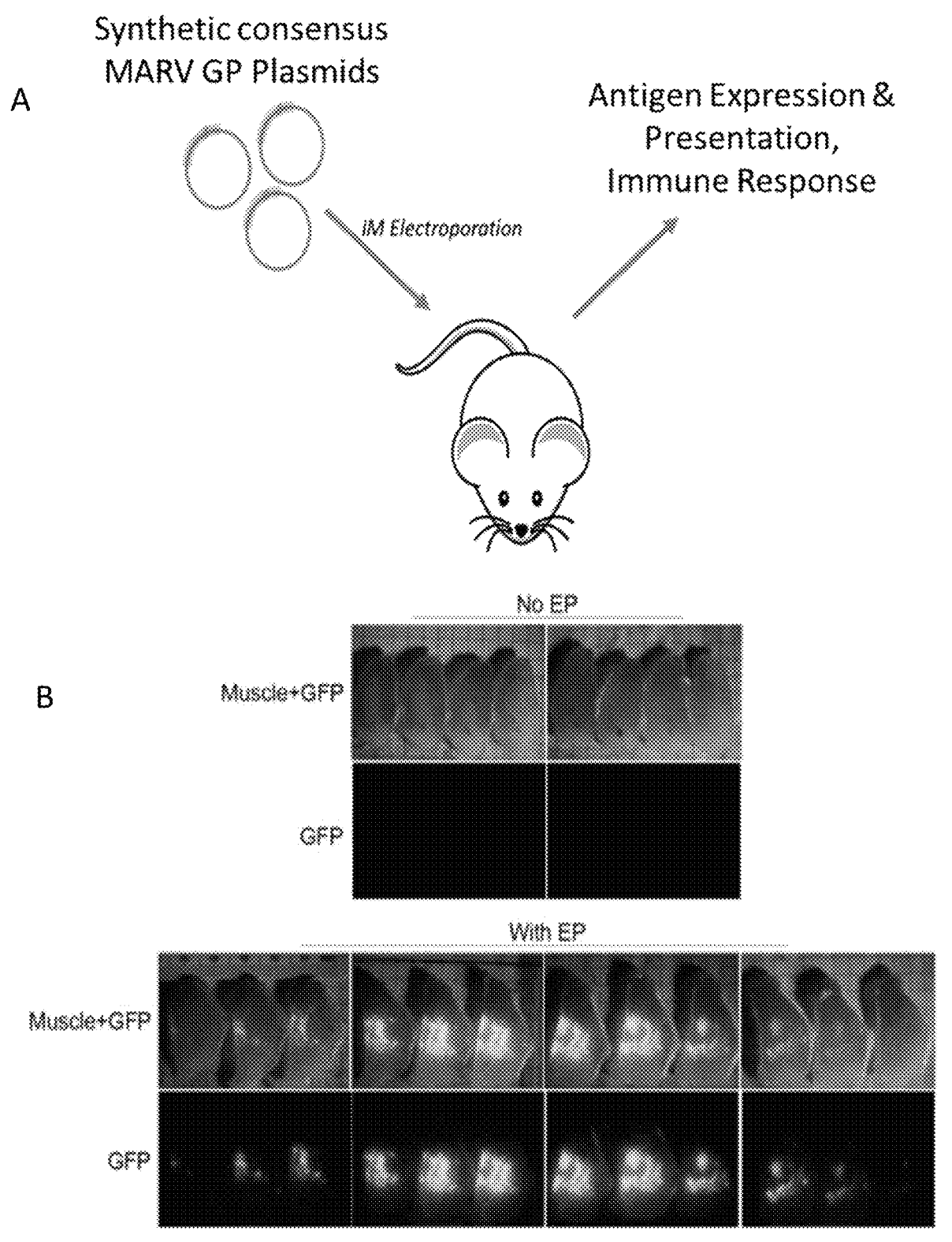

FIG. 1, comprising FIG. 1A through FIG. 1B, provides exemplary experimental data demonstrating gene expression following plasmid DNA delivery with electroporation (EP). FIG. 1A depicts the experimental design. GFP plasmids are delivered to a subject and then evaluated for GFP expression. FIG. 1B depicts images of GFP expression. GFP plasmid was delivered to rabbit muscle via IM injection without EP (top panels) or IM injection with EP (bottom panels). Muscle was harvested and sectioned into 1 mm thick sections to visualize GFP expression either under ambient light (Muscle+GFP) or under a UV lamp (GFP). GFP expression is observed only when the DNA is delivered via EP—representing a 100-1000 fold enhancement in gene delivery to the target tissue. (Sardesai et al., Curr Opin Immunol, 2011 June; 23 (3): 421-9).

FIG. 3, comprising FIG. 3A through FIG. 3B, provides exemplary experimental data demonstrating that MARV glycoprotein consensus constructs are expressed in transfected cells.

FIG. 4, comprising FIG. 4A through FIG. 4B, provides exemplary experimental data demonstrating Anti-MARV GP antibodies are generated in sera of mice vaccinated with MARV consensus GP constructs. FIG. 4A depicts the experimental desing. BALB/c mice received 40 μg plasmid DNA followed by intramuscular electroporation. Two weeks later, sera were collected for antibody analysis. FIG. 4B depicts experimental data showing that mouse IgG binding to recombinant MARV GP Angola was determined by ELISA (N=5, Mean+SD.) FIG. 4C depicts sera from mice vaccinated with MARV GP Con1 was used to stain 293T cells transfected with constructs Con1-Con3. Binding was analyzed by FACS.

FIG. 5, comprising FIG. 5A through FIG. 5E, provides exemplary experimental data demonstrating that a single vaccination induces T-Cell IFNγ response. FIG. 5A depicts vaccination schedule. FIG. 5B depicts mouse splenocytes that were stimulated with overlapping linear peptides in six different pools representing the full sequence of Angola MARV GP. IFN responses were measured by ELISPOT. (N=5 animals per group, 3 replicates per animal, Mean SD). FIG. 5C depicts splenocyotes that were stimulated with Angola MARV GP peptides and analyzed by FACS (N=5 animals per group, Mean SD). FIG. 5D depicts mouse anti-Angola-MARV GP IgG antibody endpoint binding titers in sera collected 14 days after vaccination, as measured by ELISA (N=5 animals per group, Mean SD). FIG. 5E depicts mouse anti-MARV GP antibody in pooled sera collected 14 days after vaccination, as measured by Western blot against 293T cell lysates expressing each consensus antigen (Con1, Con2, Con3), control lyate (pVax), or recombinant protein Angola MARV GP (N=5 animals). GPO is full-length GP and GP2 represents a subunit cleaved form of GP.

FIG. 6, comprising FIG. 6A through FIG. 6E, provides exemplary experimental data demonstrating the breadth of T-cell and antibody responses to diverse peptide and antigen following boosted vaccination.

FIG. 7, comprising FIG. 7A through FIG. 7E, provides exemplary experimental data demonstrating the breadth of T-cell and antibody responses to diverse peptide and antigen following boosted vaccination of combined consensus constructs. FIG. 7A depicts vaccination schedule and sample collection following dose 1 (D1) and dose 2 (D2), with co-delivery of plasmids to the same injection site or separate injection sites. FIGS. 7B and 7C depict mouse splenocytes that were stimulated with overlapping linear peptides in six different pools representing the full sequence of Angola MARV GP or Ravn MARV GP. IFN responses were measured by ELISPOT. (N=5 animals per group, 3 replicates per animal, Mean SD).

DETAILED DESCRIPTION

Figure 2:
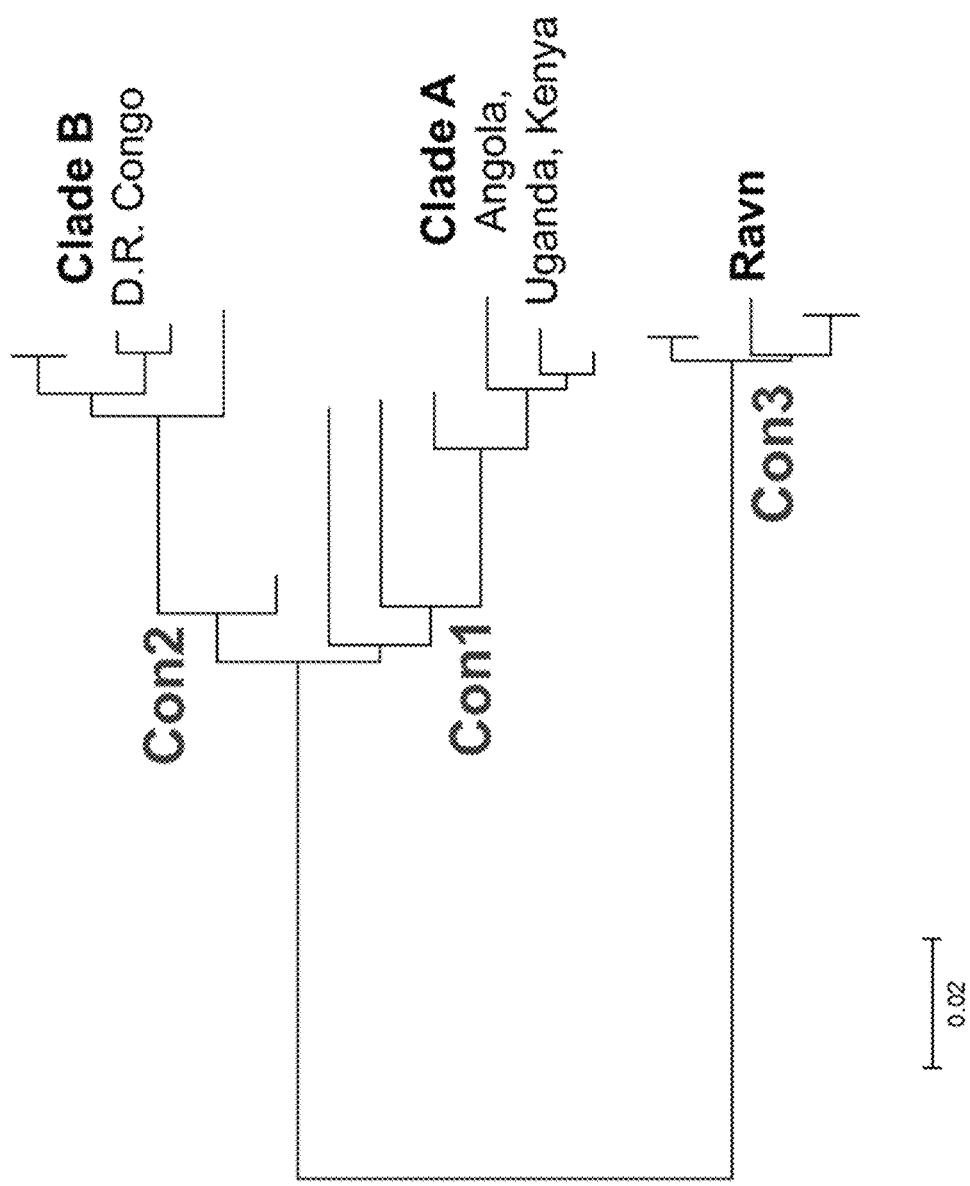
FIG. 2 provides exemplary experimental data demonstrating phylogenetic trees for the design of synthetic consensus Marburg glycoproteins. Sequences of three geographically distinct lineages of MARV virus glycoprotein (GP), including the highly divergent RAVV virus, were aligned and used to design synthetic GP Con1 (SEQ ID NO: 1/SEQ ID NO:2), Con2 (SEQ ID NO:3/SEQ ID NO:4), and Con3 (SEQ ID NO:5/SEQ ID NO: 6) antigens. These antigen sequences were synthesized and cloned into a mammalian expression plasmid, creating plasmid DNA constructs for expression of synthetic consensus antigens in vivo.

The Marburg viruses (MARV) can also be up to 90% lethal. Currently, there is only one classified species, Marburg marburgvirus (formerly Lake Victoria marburgvirus), although a recent amendment proposes that it contain two viruses including the Ravn virus (RAVV).

Synthetic DNA vaccines against Marburg marburgvirus (MARV) have been developed. The novel vaccine comprise a DNA plasmids encoding a synthetic consensus envelope glycoprotein (GP) of Marburg marburgvirus (MARV). As a vaccine candidate, an enhanced DNA (DNA)-based platform exhibits many advantages given recent advances in genetic optimization and delivery techniques (Bagarazzi M L, et al. (2012). Immunotherapy Against HPV16/18 Generates Potent TH1 and Cytotoxic Cellular Immune Responses. *Sci Transl Med* 4: 155ral38; Kee S T, Gehl J, W. L E (2011). *Clinical Aspects of Electroporation*, Springer, New York, NY.; Hirao L A, et al. (2011). Multivalent smallpox DNA vaccine delivered by intradermal electroporation drives protective immunity in nonhuman primates against lethal monkeypox challenge. *J Infect Dis* 203:95-102). As such, each GP was genetically-optimized, subcloned into modified mammalian expression vectors, and then delivered using in vivo electroporation (EP).

Preclinical studies were performed in mice using rodent-adapted viruses. Vaccination in preclinical rodent studies was highly potent, as a single delivery of consensus Marburg glycoprotein constructs to mice generates anti-MARV antibodies and robust IFNγ T cell responses.

In developing a strategy to provide protection against viruses responsible for the highest human case-fatality rates, this study focused on MARV.

In some embodiments, the strategy employs a coding sequence for a synthetic consensus glycoprotein immunogen generated from MARV. Three MARV immunogens are provided. Consensus glycoprotein Angola, D.R. Congo, or Ravn derived from three clades, were designed.

In some embodiments, the strategy employs coding sequences for a single synthetic consensus glycoprotein immunogen generated from MARV. In some embodiments, the strategy employs coding sequences for multiple synthetic consensus glycoprotein immunogens generated from MARV.

As a candidate for vaccines, DNA vaccines exhibit a multitude of advantages including rapid and inexpensive up-scale production, stability at room temperature, and ease of transport, all of which further enhance this platform from an economic and geographic perspective. Due to the synthetic nature of the plasmids, antigen sequences can be quickly and easily modified in response to newly emergent species and/or expanded to include additional vaccine components and/or regimen for rapid response during outbreak settings. For example, the MARV strategies herein can be easily expanded for greater coverage by the co-administration of additional plasmids encoding consensus MARV GP (MGP) immunogens for other phylogenetic clusters.

While 'first-generation' DNA vaccines were poorly immunogenic, recent technological advances have dramatically improved their immunogenicity in clinical trials. Optimization of plasmid DNA vectors and their encoded antigen genes have led to increases in in vivo immunogenicity. Cellular uptake and subsequent antigen expression are substantially amplified when highly-concentrated plasmid vaccine formulations are administered with in vivo electroporation, a technology that uses brief square-wave electric pulses within the vaccination site to drive plasmids into transiently permeabilized cells. In theory, a cocktail of DNA plasmids could be assembled for directing a highly-specialized immune response against any number of variable antigens. Immunity can be further directed by co-delivery with plasmid molecular adjuvants encoding species-specific cytokine genes as well as 'consensus-engineering' of the antigen amino acid sequences to help bias vaccine-induced immunity towards particular strains. This strategy has been shown to enhance protection among divergent strains of influenza virus and HIV. Due in parts to these technological advancements, immunization regimens including these DNA vaccines are highly versatile and extremely customizable.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein may mean any molecule added to the DNA plasmid vaccines described herein to enhance antigenicity of the one or more consensus filovirus immunogens encoded by the DNA plasmids and encoding nucleic acid sequences described hereinafter.

"Antibody" may mean an antibody of classes IgG, IgM, IgA, IgD or IgE, or fragments, fragments or derivatives thereof, including Fab, F(ab') 2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab') 2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Antigen" refers to proteins that have the ability to generate an immune response in a host. An antigen may be recognized and bound by an antibody. An antigen may originate from within the body or from the external environment.

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered. In some embodiments, the coding sequence may optionally further comprise a start codon that encodes an N terminal methionine or a signal peptide such as an IgE or IgG signal peptide.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "consensus sequence" as used herein may mean a synthetic nucleic acid sequence, or corresponding polypeptide sequence, constructed based on analysis of an alignment of multiple subtypes of a particular filovirus antigen, that can be used to induce broad immunity against multiple subtypes or serotypes of a particular filovirus antigen.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a percentage of a full length polypeptide sequence or nucleic acid sequence. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the full length of the parental nucleic acid sequence or amino acid sequence or variant thereof.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more filovirus consensus antigen via the provided DNA plasmid vaccines. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human.

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of +2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within +2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleotide sequence that is substantially identical over the full length of the full gene sequence or a fragment thereof. The nucleotide sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Description

The invention provides an optimized consensus sequence encoding a Marburgvirus antigen. In one embodiment, the Marburgvirus antigen encoded by the optimized consensus sequence is capable of eliciting an immune response in a mammal. In one embodiment, the Marburgvirus antigen encoded by the optimized consensus sequence can comprise an epitope(s) that makes it particularly effective as an immunogen against which an immune response can be induced.

The optimized consensus sequence can be a consensus sequence derived from two or more Marburgvirus proteins. The optimized consensus sequence can comprise a consensus sequence and/or modification(s) for improved expression. Modification can include codon optimization, RNA optimization, addition of a kozak sequence for increased translation initiation, and/or the addition of an immunoglobulin leader sequence to increase immunogenicity. The Marburgvirus antigen encoded by the optimized consensus sequence can comprise a signal peptide such as an immunoglobulin signal peptide, for example, but not limited to, an immunoglobulin E (IgE) or immunoglobulin (IgG) signal peptide. In some embodiments, the antigen encoded by the optimized consensus sequence can comprise a hemagglutinin (HA) tag. The antigen encoded by the optimized consensus sequence can be designed to elicit stronger cellular and/or humoral immune responses than a corresponding non-optimized antigen.

Provided herein are Marburgvirus immunogens that can be used to induce broad immunity against multiple subtypes or serotypes of Marburgvirus. In one embodiment, the present invention provides an immunogenic composition comprising one or more nucleic acid molecules that are capable of generating in a mammal an immune response against a Marburgvirus. The present invention also provides isolated nucleic acid molecules that are capable of generating in a mammal an immune response against a Marburgvirus. In one embodiment, the nucleic acid molecule comprises an optimized nucleotide sequence encoding a consensus Marburgvirus immunogen.

Consensus amino acid sequences for Marburgvirus immunogens include SEQ ID NO: 2, SEQ ID NO:4, SEQ ID NO:6, variants thereof and fragments of SEQ ID NO:2, SEQ ID NO:4, SEQ ID NO:6 and variants thereof.

In one embodiment, the invention provides compositions comprising a nucleic acid molecule comprising a nucleotide sequence that encodes a consensus Marburg marburgvirus envelope glycoprotein immunogen. Nucleic acid sequences that encode a first consensus Marburg marburgvirus envelope glycoprotein immunogen (SEQ ID NO:1), a nucleic acid sequence that encodes a second consensus Marburg marburgvirus envelope glycoprotein immunogen (SEQ ID NO:3), and a nucleic acid sequence that encodes a third consensus Marburg marburgvirus envelope glycoprotein immunogen (SEQ ID NO:5) are disclosed.

In one embodiment, a nucleotide sequence which encodes SEQ ID NO:2, Marburg marburgvirus envelope glycoprotein immunogen Con1, is SEQ ID NO:1.

In one embodiment, a nucleotide sequence which encodes SEQ ID NO:4, Marburg marburgvirus envelope glycoprotein immunogen Con2, is SEQ ID NO:3.

In one embodiment, a nucleotide sequence which encodes SEQ ID NO:6, Marburg marburgvirus envelope glycoprotein immunogen Con3, is SEQ ID NO:5.

In one embodiment, an optimized consensus encoded Marburgvirus antigen is operably linked to one or more regulatory elements. In one embodiment, a regulatory element is a leader sequence. In one embodiment, the leader sequence is an IgE leader sequence. In one embodiment, the IgE leader sequence has an amino acid sequence as set forth in SEQ ID NO: 8. Therefore in one embodiment, the invention relates to an amino acid sequence as set forth in SEQ ID NO:2, SEQ ID NO:4 or SEQ ID NO:6 operably linked to an amino acid sequence as set forth in SEQ ID NO:8. In one embodiment, the invention relates to a nucleotide sequence encoding an amino acid sequence as set forth in SEQ ID NO:2, SEQ ID NO: 4 or SEQ ID NO:6 operably linked to a nucleotide sequence encoding SEQ ID NO:8.

In one embodiment, a regulatory element is a start codon. Therefore, in one embodiment, the invention relates to a nucleic acid sequence as set forth in SEQ ID NO:1, SEQ ID NO:3 or SEQ ID NO:5, or a fragment or homolog thereof, operably linked to a nucleotide sequence comprising a start codon at the 5' terminus. In one embodiment, the invention relates to an amino acid sequence as set forth in SEQ ID NO:2, SEQ ID NO:4 or SEQ ID NO:6 or a fragment or homolog thereof, operably linked to an amino acid encoded by a start codon (e.g., a Methionine) at the N-terminus.

In one embodiment, a regulatory element is at least one stop codon. Therefore, in one embodiment, the invention relates to a nucleic acid sequence as set forth in SEQ ID NO: 1, SEQ ID NO:3 or SEQ ID NO:5 or a fragment or homolog thereof, operably linked to a nucleotide sequence comprising at least one stop codon at the 3' terminus. In one embodiment, the nucleotide sequence is operably linked to two stop codons to increase the efficiency of translational termination.

In one embodiment, nucleic acid molecule can encode a peptide having the amino acid sequence set forth in SEQ ID NO:2, SEQ ID NO:4, or SEQ ID NO: 6. In one embodiment, the nucleic acid molecule comprises the nucleotide sequence set forth in SEQ ID NO: 1, SEQ ID NO: 3, or SEQ ID NO: 5. In some embodiments, the sequence can be the nucleotide sequence having at least about 90%, 91%, 92%, 93%, 94%, 95%, 96%, 97%, 98%, 99% or 100% identity over an entire length of the nucleotide sequence set forth in SEQ ID NO: 1, SEQ ID NO: 3, or SEQ ID NO: 5. In other embodiments, sequence can be the nucleotide sequence that encodes the amino acid sequence having at least about 90%, 91%, 92%, 93%, 94%, 95%, 96%, 97%, 98%, 99%, or 100% identity over an entire length of the amino acid sequence set forth in SEQ ID NO:2, SEQ ID NO:4, or SEQ ID NO: 6.

In some embodiments, the nucleic acid molecule comprises an RNA sequence that is a transcript from a DNA sequence having at least about 96%, 97%, 98%, 99% or 100% identity over an entire length of the nucleic acid sequence set forth in SEQ ID NO: 1, SEQ ID NO: 3, or SEQ ID NO: 5. In some embodiments, the nucleic acid molecule comprises an RNA sequence that encodes an amino acid sequence having at least about 96%, 97%, 98%, 99% or 100% identity over an entire length of the amino acid sequence set forth in SEQ ID NO: 2, SEQ ID NO:4, or SEQ ID NO: 6.

In some embodiments, the nucleic acid sequence may encode a full length consensus Marburg marburgvirus envelope glycoprotein immunogen. Nucleic acid molecules may comprise a sequence that encodes SEQ ID NO:2, SEQ ID NO:4 or SEQ ID NO: 6. Nucleic acid sequence may comprise SEQ ID NO:1, SEQ ID NO:3 or SEQ ID NO:5. Nucleic acid sequence may optionally comprise coding sequences that encode a signal peptide such as for example an IgE or IgG signal peptide.

The consensus-Marburgvirus antigen can be a peptide having the amino acid sequence set forth in SEQ ID NO:2, SEQ ID NO:4 or SEQ ID NO:6. In some embodiments, the antigen can have an amino acid sequence having at least about 90%, 91%, 92%, 93%, 94%, 95%, 96%, 97%, 98%, 99%, or 100% identity over an entire length of the amino acid sequence set forth in SEQ ID NO:2, SEQ ID NO:4 or SEQ ID NO:6.

Immunogenic fragments of SEQ ID NO:2, SEQ ID NO:4 or SEQ ID NO:6 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of the full length of SEQ ID NO:2, SEQ ID NO:4 or SEQ ID NO: 6. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:2, SEQ ID NO:4 or SEQ ID NO:6, can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4 or SEQ ID NO:6. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

In one embodiment, an immunogenic fragment of a nucleic acid molecule encodes at least one immunodominant or sub-immunodominant epitope of a full length optimized consensus Marburgvirus antigen.

Some embodiments relate to immunogenic fragments of SEQ ID NO: 1, SEQ ID NO: 3 or SEQ ID NO:5 comprising at least 60%, at least 65%, at least 70%, at least 75%, at least 80%, at least 85%, at least 90%, at least 95%, at least 96%, at least 97%, at least 98% or at least 99% of the full length of SEQ ID NO:1, SEQ ID NO:3 or SEQ ID NO:5. Immunogenic fragments can be at least 96%, at least 97% at least 98% or at least 99% homologous to fragments of SEQ ID NO:1, SEQ ID NO:3 or SEQ ID NO:5. In some embodiments, immunogenic fragments include sequences that encode a leader sequence, such as for example an immunoglobulin leader, such as the IgE leader. In some embodiments, fragments are free of coding sequences that encode a leader sequence.

In one embodiment, the nucleic acid molecule comprises a sequence at least 90% homologous to SEQ ID NO:1, SEQ ID NO:3 or SEQ ID NO:5.

In one embodiment, the nucleic acid sequence comprises an RNA sequence encoding a consensus Marburgvirus immunogen sequence described herein. For example, nucleic acids may comprise an RNA sequence encoding one or more of SEQ ID NO:2, SEQ ID NO: 4 or SEQ ID NO:6, a variant thereof, a fragment thereof or any combination thereof.

In some embodiments, the nucleic acid molecule includes a sequence that encodes for a Marburgvirus antigen minus an IgE leader sequence on the N-terminal end of the coding sequence. In some embodiments, the DNA nucleic acid molecule further comprises an IgE leader sequence attached to an N-terminal end of the coding sequence and operably linked to the promoter.

The nucleic acid molecule can further include a polyadenylation sequence attached to the C-terminal end of the coding sequence. In one embodiment, the nucleic acid molecule is codon optimized.

Immunogenic Compositions

Immunogenic compositions, such as vaccines, are provided comprising an optimized consensus sequence, an optimized consensus-encoded antigen, a fragment thereof, a variant thereof, or a combination thereof. The immunogenic composition can significantly induce an immune response of a subject administered with the immunogenic composition against the Marburgvirus immunogen.

The immunogenic composition can be a DNA vaccine, an RNA vaccine, a peptide vaccine, or a combination vaccine. The vaccine can include an optimized consensus nucleotide sequence encoding an antigen. The nucleotide sequence can be DNA, RNA, cDNA, a variant thereof, a fragment thereof, or a combination thereof. The nucleotide sequence can also include additional sequences that encode linker, leader, or tag sequences that are linked to the antigen by a peptide bond. The peptide vaccine can include an antigen, a variant thereof, a fragment thereof, or a combination thereof. The combination DNA and peptide vaccine can include the above described optimized consensus nucleotide sequence and the encoded antigen.

The vaccine can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose.

The compositions may comprise a plurality of copies of a single nucleic acid molecule such a single plasmid, a plurality of copies of two or more different nucleic acid molecules such as two or more different plasmids. For example a composition may comprise plurality of two, three, four, five, six, seven, eight, nine or ten or more different nucleic acid molecules. Such compositions may comprise plurality of two, three, four, five, six, or more different plasmids.

Compositions may comprise nucleic acid molecules, such as plasmids, that collectively contain coding sequence for a single consensus Marburg marburgvirus envelope glycoprotein immunogen. Compositions may comprise nucleic acid molecules, such as plasmids, that collectively contain coding sequence for multiple consensus Marburg marburgvirus envelope glycoprotein immunogens.

Compositions may comprise nucleic acid sequence that encodes the combination of the first consensus Marburg marburgvirus envelope glycoprotein immunogen, the second consensus Marburg marburgvirus envelope glycoprotein immunogen and the third consensus Marburg marburgvirus envelope glycoprotein immunogen.

Each coding sequence for each consensus Marburg marburgvirus envelope glycoprotein immunogen is preferably included on a separate plasmid.

Accordingly, compositions that comprise nucleic acid sequence that encode multiple consensus Marburg marburgvirus envelope glycoprotein immunogens may be on a single plasmid but are preferably on two or more separate plasmids.

Provided herein is an immunogenic composition capable of generating in a mammal an immune response against Marburgvirus. The immunogenic composition may comprise each plasmid as discussed above. The immunogenic composition may comprise a plurality of the plasmids, or combinations thereof. The immunogenic composition may be provided to induce a therapeutic or prophylactic immune response.

Immunogenic compositions may be used to deliver nucleic acid molecules that encode one or more consensus Marburg marburgvirus envelope glycoprotein immunogen. Immunogenic compositions are preferably compositions comprising plasmids.

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid immunogenic compositions may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. or a combination thereof. In some embodiments adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/

024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The immunogenic composition may further comprise a genetic vaccine facilitator agent as described in U.S. Ser. No. 021,579 filed Apr. 1, 1994, which is fully incorporated by reference.

The immunogenic composition may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

The immunogenic composition may be formulated according to the mode of administration to be used. An injectable immunogenic composition pharmaceutical composition may be sterile, pyrogen free and particulate free. An isotonic formulation or solution may be used. Additives for isotonicity may include sodium chloride, dextrose, mannitol, sorbitol, and lactose. The immunogenic composition may comprise a vasoconstriction agent. The isotonic solutions may include phosphate buffered saline. Immunogenic composition may further comprise stabilizers including gelatin and albumin. The stabilizing may allow the formulation to be stable at room or ambient temperature for extended periods of time such as LGS or polycations or polyanions to the immunogenic composition formulation.

The immunogenic composition may be stable at room temperature (25° C.) for more than 1 week, in some embodiments for more than 2 weeks, in some embodiments for more than 3 weeks, in some embodiments for more than 4 weeks, in some embodiments for more than 5 weeks, and in some embodiments for more than 6 weeks. In some embodiments, the vaccine is stable for more than one month, more than 2 months, more than 3 months, more than 4 months, more than 5 months, more than 6 months, more than 7 months, more than 8 months, more than 9 months, more than 10 months, more than 11 months, or more than 12 months. In some embodiments, the vaccine is stable for more than 1 year, more than 2 years, more than years, or more than 5 years. In one embodiment, the immunogenic composition is stable under refrigeration (2-8° C.). Accordingly, in one embodiment, the immunogenic composition does not require frozen cold-chain. An immunogenic composition is stable if it retains its biological activity for a sufficient period to allow its intended use (e.g., to generate an immune response in a subject). For example, for immunogenic compositions that are to be stored, shipped, etc., it may be desired that the immunogenic compositions remain stable for months to years.

Immune Response

The immunogenic composition can induce an immune response in the subject administered the composition. The induced immune response can be specific for a Marburgvirus antigen. The induced immune response can be reactive with a Marburgvirus antigen related to the optimized consensus-encoded antigen. In various embodiments, related antigens include antigens having amino acid sequences having at least 90%, at least 91%, at least 92%, at least 93%, at least 94%, at least 95%, at least 96%, at least 97%, at least 98%, at least 99%, or 100% homology to the amino acid sequence of the optimized consensus-encoded antigen. In various embodiments, related antigens include antigens encoded by nucleotide sequences having at least 90%, at least 91%, at least 92%, at least 93%, at least 94%, at least 95%, at least 96%, at least 97%, at least 98%, at least 99%, or 100% homology to the optimized consensus nucleotide sequences disclosed herein.

The immunogenic composition can induce a humoral immune response in the subject administered the immunogenic composition. The induced humoral immune response can be specific for a Marburgvirus antigen. The induced humoral immune response can be reactive with the Marburgvirus antigen related to the optimized consensus-encoded antigen. The humoral immune response can be induced in the subject administered the immunogenic composition by about 1.5-fold to about 16-fold, about 2-fold to about 12-fold, or about 3-fold to about 10-fold. The humoral immune response can be induced in the subject administered the immunogenic composition by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized Marburgvirus antigen.

The humoral immune response induced by the immunogenic composition can include an increased level of neutralizing antibodies associated with the subject administered the immunogenic composition as compared to a subject not administered the immunogenic composition. The neutralizing antibodies can be specific for a Marburgvirus antigen related to the optimized consensus-encoded antigen. The neutralizing antibodies can be reactive with the Marburgvirus antigen genetically related to the optimized consensus antigen. The neutralizing antibodies can provide protection against and/or treatment of tumor growth, metastasis or tumor associated pathologies in the subject administered the immunogenic composition.

The humoral immune response induced by the immunogenic composition can include an increased level of IgG antibodies associated with the subject administered the immunogenic composition as compared to a subject not administered the immunogenic composition. These IgG antibodies can be specific for the Marburgvirus antigen genetically related to the optimized consensus antigen. These IgG antibodies can be reactive with the Marburgvirus antigen genetically related to the optimized consensus antigen. The level of IgG antibody associated with the subject administered the immunogenic composition can be increased by about 1.5-fold to about 16-fold, about 2-fold to about 12-fold, or about 3-fold to about 10-fold as compared to the subject not administered the immunogenic composition. The level of IgG antibody associated with the subject administered the immunogenic composition can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to a subject not administered the immunogenic composition or a subject administered a non-optimized Marburgvirus antigen.

The immunogenic composition can induce a cellular immune response in the subject administered the immunogenic composition. The induced cellular immune response can be specific for a Marburgvirus antigen related to the optimized consensus-encoded antigen. The induced cellular immune response can be reactive to the Marburgvirus antigen related to the optimized consensus-encoded antigen. The induced cellular immune response can include eliciting a CD8$^+$ T cell response. The elicited CD8$^+$ T cell response can be reactive with the Marburgvirus antigen genetically related to the optimized consensus antigen. The elicited CD8$^+$ T cell response can be polyfunctional. The induced cellular immune response can include eliciting a CD8$^+$ T cell response, in which the CD8$^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased CD8$^+$ T cell response associated with the subject administered the immunogenic composition as compared to the subject not administered the immunogenic composition. The CD8$^+$ T cell response associated with the subject administered the immunogenic composition can be increased by about 2-fold to about 30-fold, about 3-fold to about 25-fold, or about 4-fold to about 20-fold as compared to the subject not administered the immunogenic composition. The CD8$^+$ T cell response associated with the subject administered the immunogenic composition can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to a subject not administered the immunogenic composition or a subject administered a non-optimized Marburgvirus antigen.

The induced cellular immune response can include an increased frequency of CD107a/IFN$\gamma$/T-bet triple-positive CD8 T cells that are reactive against the Marburgvirus antigen. The frequency of CD107a/IFN$\gamma$/T-bet triple-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized Marburgvirus antigen.

The induced cellular immune response can include an increased frequency of CD107a/IFN$\gamma$ double-positive CD8 T cells that are reactive against the Marburgvirus antigen. The frequency of CD107a/IFN$\gamma$ double-positive CD8 T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to a subject not administered the immunogenic composition or a subject administered a non-optimized Marburgvirus antigen.

The cellular immune response induced by the immunogenic composition can include eliciting a CD4$^+$ T cell response. The elicited CD4$^+$ T cell response can be reactive with the Marburgvirus antigen genetically related to the optimized consensus antigen. The elicited CD4$^+$ T cell response can be polyfunctional. The induced cellular immune response can include eliciting a CD4$^+$ T cell response, in which the CD4$^+$ T cells produce IFN-$\gamma$, TNF-$\alpha$, IL-2, or a combination of IFN-$\gamma$ and TNF-$\alpha$.

The induced cellular immune response can include an increased frequency of CD4$^+$ T cells that produce IFN-$\gamma$. The frequency of CD4$^+$IFN-$\gamma_+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to a subject not administered the immunogenic composition or a subject administered a non-optimized Marburgvirus antigen.

The induced cellular immune response can include an increased frequency of CD4$^+$ T cells that produce TNF-$\alpha$. The frequency of CD4$_+$TNF-$\alpha_+$ T cells associated with the subject administered the immunogenic composition can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to a subject not administered the immunogenic composition or a subject administered a non-optimized Marburgvirus antigen.

The induced cellular immune response can include an increased frequency of CD4+ T cells that produce both IFN-γ and TNF-α. The frequency of CD4 IFN-γ+TNF-α+ associated with the subject administered the immunogenic composition can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to a subject not administered the immunogenic composition or a subject administered a non-optimized Marburgvirus antigen.

The immunogenic composition can further induce an immune response when administered to different tissues such as the muscle or skin. The immunogenic composition can further induce an immune response when administered via electroporation, or injection, or subcutaneously, or intramuscularly.

Vector

The nucleic acid sequence construct described above can be placed in one or more vectors. Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to one of SEQ ID NOs: 1, 3 or 5. In another embodiment, the nucleotide sequence comprises an RNA sequence transcribed by a DNA sequence encoding a polypeptide sequence of SEQ ID NOs: 2, 4 or 6 or a variant thereof or a fragment thereof. Accordingly, in one embodiment, the invention provides an RNA molecule encoding one or more of the DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(4) Circular and Linear Vector

The one or more vectors may be circular plasmid, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be pcrM2. The LEC can be perNP. perNP and pcrMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939, 792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

Multiple Vectors

The immunogenic composition may comprise a plurality of copies of a single nucleic acid molecule such a single plasmid, or a plurality of copies of two or more different nucleic acid molecules such as two or more different plasmids. For example an immunogenic composition may comprise plurality of two, three, four, five, six, seven, eight, nine or ten or more different nucleic acid molecules. Such compositions may comprise plurality of two, three, four, five, six, or more different plasmids.

Immunogenic compositions may comprise nucleic acid molecules, such as plasmids, that collectively contain coding sequence for a Marburgvirus antigen. Immunogenic compositions may comprise nucleic acid molecules, such as plasmids, that collectively contain coding sequence for multiple antigens. In one embodiment, the antigens are a Marburgvirus antigen and one or more additional cancer antigen. Immunogenic compositions may comprise nucleic acid molecules, such as plasmids, that collectively contain coding sequence for one or more antigen and one or more cancer antigen.

Methods

Also provided herein is a method of treating, protecting against, and/or preventing disease in a subject in need thereof by administering the immunogenic composition to the subject. Administration of the immunogenic composition to the subject can induce or elicit an immune response in the subject. The induced immune response can be used to treat, prevent, and/or protect against disease, for example, Marburg virus infection or hemorrhagic fever associated with Marburg virus infection.

Provided herein is a method for delivering the immunogenic composition for providing genetic constructs and proteins of the consensus antigen which comprise epitopes that make them particular effective against Marburgvirus, against which an immune response can be induced. The method of delivering the immunogenic composition or vaccination may be provided to induce a therapeutic and prophylactic immune response. The vaccination process may generate in the mammal an immune response against Marburgvirus. The immunogenic composition may be delivered to an individual to modulate the activity of the mammal's immune system and enhance the immune response. The delivery of the immunogenic composition may be the transfection of the consensus antigen as a nucleic acid molecule that is expressed in the cell and delivered to the surface of the cell upon which the immune system recognized and induces a cellular, humoral, or cellular and humoral response. The delivery of the immunogenic composition may be used to induce or elicit and immune response in mammals against Marburgvirus by administering to the mammals the immunogenic composition as discussed above.

Upon delivery of the immunogenic composition and plasmid into the cells of the mammal, the transfected cells will express and secrete consensus antigens for each of the plasmids injected from the immunogenic composition. These proteins will be recognized as foreign by the immune system and antibodies will be made against them. These antibodies will be maintained by the immune system and allow for an effective response to subsequent infections by Marburgvirus.

The immunogenic composition may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced humoral immune response can include IgG antibodies and/ or neutralizing antibodies that are reactive to the antigen. The induced cellular immune response can include a $CD8^+$ T cell response, which is induced by about 2-fold to about 30-fold, about 3-fold to about 25-fold, or about 4-fold to about 20-fold.

The immunogenic composition dose can be between 1 µg to 10 mg active component/kg body weight/time, and can be 20 µg to 10 mg component/kg body weight/time. The immunogenic composition can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of immunogenic composition doses for effective treatment can be 1, 2, 3, 4, 5, 6, 7, 8, 9, or 10.

The immunogenic composition can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration.

The immunogenic composition can be administered prophylactically or therapeutically. In prophylactic administration, the immunogenic compositions can be administered in an amount sufficient to induce an immune response. In therapeutic applications, the immunogenic compositions are administered to a subject in need thereof in an amount sufficient to elicit a therapeutic effect. An amount adequate to accomplish this is defined as "therapeutically effective dose." Amounts effective for this use will depend on, e.g., the particular composition of the immunogenic composition regimen administered, the manner of administration, the stage and severity of the disease, the general state of health of the subject, and the judgment of the prescribing physician.

The immunogenic composition can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the immunogenic composition can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The immunogenic composition can be delivered via a variety of routes. Typical delivery routes include parenteral administration, e.g., intradermal, intramuscular or subcutaneous delivery. Other routes include oral administration, intranasal, and intravaginal routes. For the DNA of the immunogenic composition in particular, the immunogenic composition can be delivered to the interstitial spaces of tissues of an individual (Felgner et al., U.S. Pat. Nos. 5,580,859 and 5,703,055, the contents of all of which are incorporated herein by reference in their entirety). The immunogenic composition can also be administered to muscle, or can be administered via intradermal or subcutaneous injections, or transdermally, such as by iontophoresis. Epidermal administration of the immunogenic composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The immunogenic composition can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the immunogenic composition.

The immunogenic composition can be a liquid preparation such as a suspension, syrup or elixir. The immunogenic composition can also be a preparation for parenteral, subcutaneous, intradermal, intramuscular or intravenous administration (e.g., injectable administration), such as a sterile suspension or emulsion.

The immunogenic composition can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

Combination Treatments

The immunogenic composition may be administered in combination with other proteins and/or genes encoding CCL20, α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the immunogenic composition is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The immunogenic composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The immunogenic composition may be administered by traditional syringes, needleless injection devices, "microprojectile bombardment gone guns", or other physical methods such as electroporation ("EP"), "hydrodynamic method", or ultrasound.

The plasmid of the immunogenic composition may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

Electroporation

Administration of the immunogenic composition via electroporation of the plasmids of the immunogenic composition may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (VGX Pharmaceuticals, Blue Bell, PA) or Elgen electroporator (Genetronics, San Diego, CA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA immunogenic compositions include those provided in co-pending and co-owned U.S. patent application Ser. No. 11/874,072, filed Oct. 17, 2007, which claims the benefit under 35 USC 119 (e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

Generation of Antigens In Vitro and Ex Vivo

In one embodiment, the optimized consensus Marburgvirus antigen is generated in vitro or ex vivo. For example, in one embodiment, a nucleic acid encoding an optimized consensus Marburgvirus antigen can be introduced and expressed in an in vitro or ex vivo cell.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

EXAMPLES

The present invention is further illustrated in the following Example. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: DNA Vaccine Targeting Marburg Virus

A DNA vaccine targeting Marburg (MARV) virus has been developed. Optimized synthetic consensus MARV glycoprotein (GP) sequences representing each of three diverse lineages of Marburg virus were individually cloned into mammalian expression-plasmid DNA and delivered to mice via intramuscular electroporation. Two weeks following a single immunization, DNA vaccine constructs generated robust antibody and T-cell responses against Marburg GP.

Methods

MARV GP Sequences & Cloning: Published MARV GP amino acid sequences were aligned to generate synthetic consensus antigens. Sequences were DNA codon-optimized and RNA optimized, and cloned into a modified pVax-1 (Invitrogen) mammalian expression plasmid.

Transfections: Approx. $0.5 \times 10^6$ 293T cells were transfected with 0.5 µg plasmid DNA using GeneJammer (Agilent Technologies). Cell supernatants and lysates were collected 48 hours later.

DMAb Electroporation: BALB/c mice received 40 µg of plasmid DNA delivered i.m. to the quadriceps followed by EP with a CELLECTRA® 3P device (Inovio Pharmaceuticals, Plymouth Meeting, PA).

ELISA: 96 well plates were coated with recombinant Angola MARV GP (IBT Bioservices). Mouse sera were added at indicated dilutions. Bound antibody was detected with an anti-mouse-IgG secondary antibody conjugated to HRP.

Western Blot: 293T cell lysates were run on a 4-12% BisTris gel and transferred to PVDF. Antigen was detected with a rabbit anti-MARV GP Angola antibody (IBT Bioservices), followed with an anti-rabbit secondary 800 nm fluorescent antibody (Licor).

Flow Cytometry & ELISPOT: 293T cells were suspended using 2 mM EDTA. Sera and/or rabbit anti-MARV GP Angola antibody were added for 1 hour, followed by secondary anti-mouse or anti-rabbit FITC-conjugated antibody. Splenocytes were harvested and simulated for 5 hours with MARV GP Angola peptides. Data were acquired on a BD LSR and analyzed in FlowJo. Cells were gated on singlets, live/dead, lymphocytes, $CD3^+$. Separate splenocytes were counted and plated to 96 well mouse IFN ELISPOT plates (Mabtech), followed by overnight stimulation with overlapping linear peptide pools.

Results

Vaccine Construction and Expression

Figure 3A:
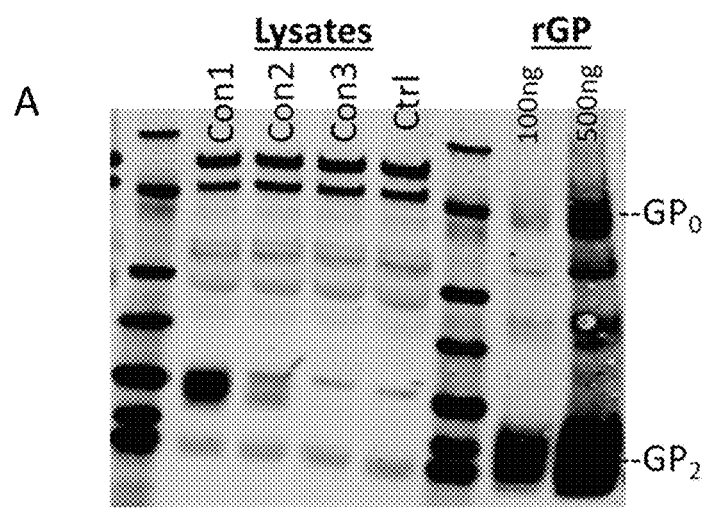
FIG. 3A depicts a western blot analysis of MARV glycoprotein expression in 293T cells transfected with MARV GP consensus DNA constructs (Con1-Con3) or empty plasmid (Ctrl). Anti-MARV-Angola-GP antibody was used to detect GP expression. The western blot shows reduced cell lysates, compared to purified recombinant Angola MARV GP (rGP) loaded onto the gel in two concentrations.
Figure 3B:
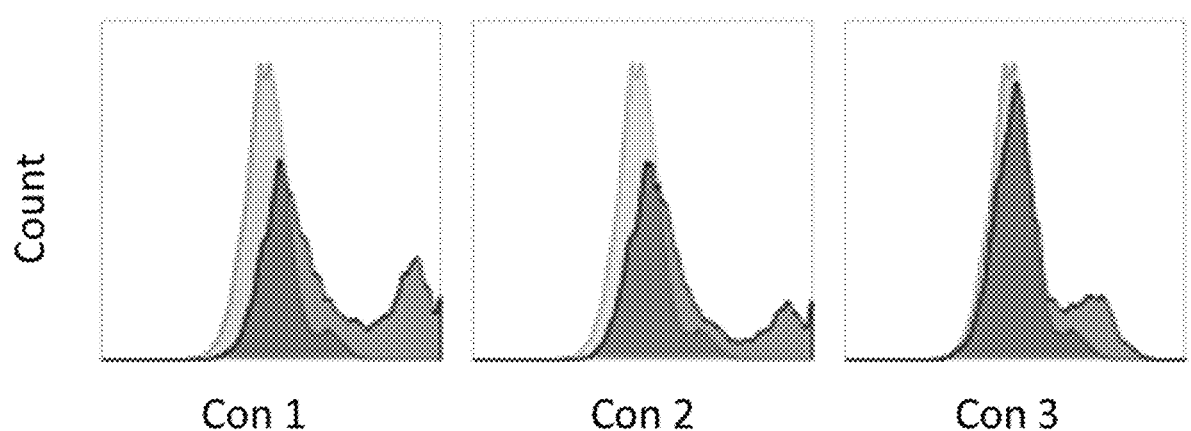
FIG. 3B depicts FACS analysis of MARV GP consensus expression (black) on the cell surface versus expression on cells transfected with empty plasmid (gray).
Figure 6A:
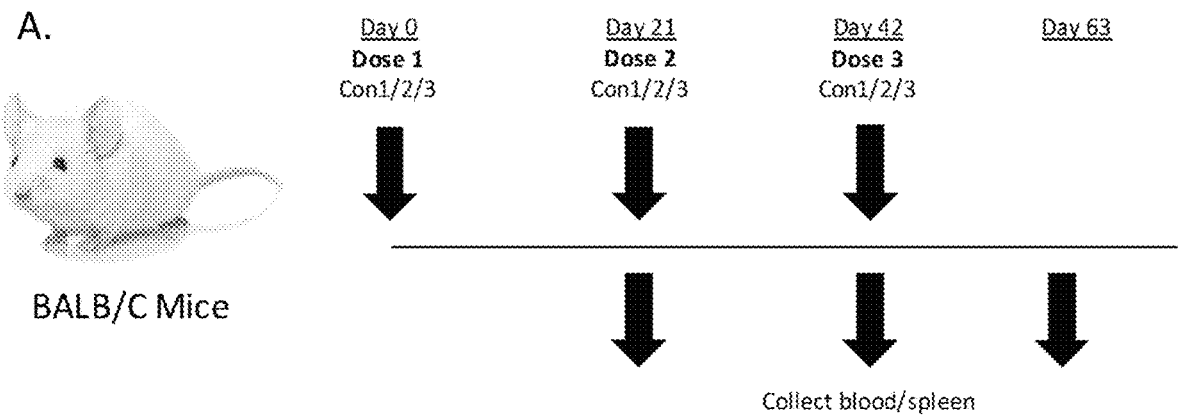
FIG. 6A depicts the vaccination schedule and sample collection used in the experiments.
Figure 6B:
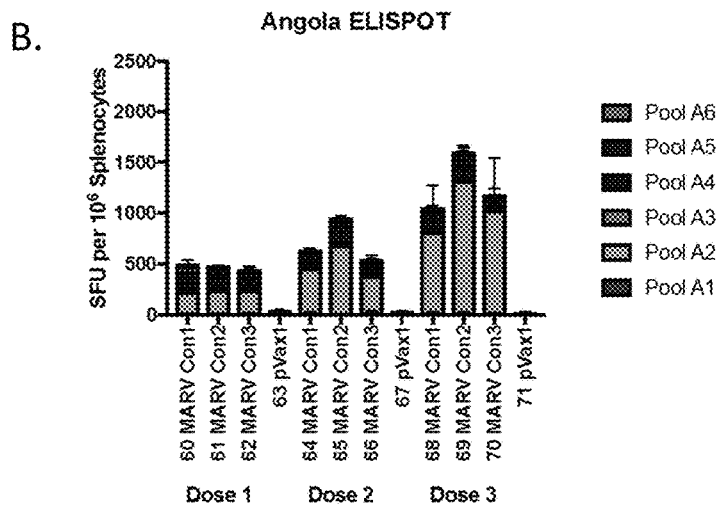
FIG. 6B depicts mouse splenocytes that were stimulated with overlapping linear peptides in six different pools representing the full sequence of Angola MARV GP. IFN responses were measured by ELISPOT. (N=5 animals per group, 3 replicates per animal, Mean SD).
Figure 6C:
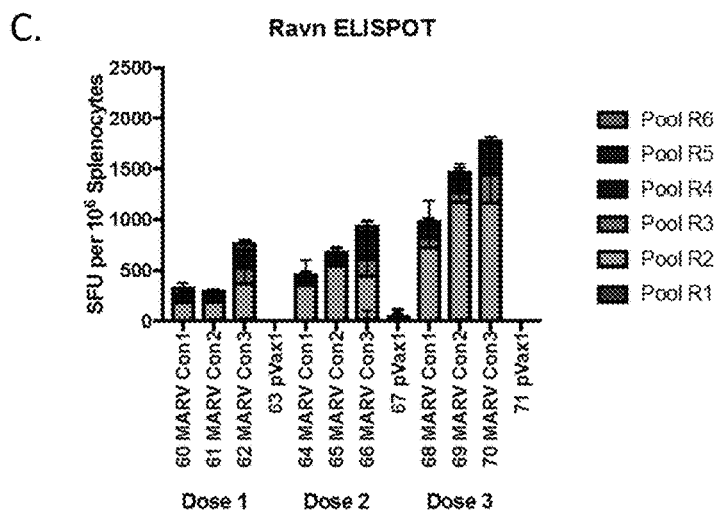
FIG. 6C depicts mouse splenocytes that were stimulated with overlapping linear peptides in six different pools representing the full sequence of Ravn MARV GP. IFN responses were measured by ELISPOT. (N=5 animals per group, 3 replicates per animal, Mean SD).
Figure 6D:
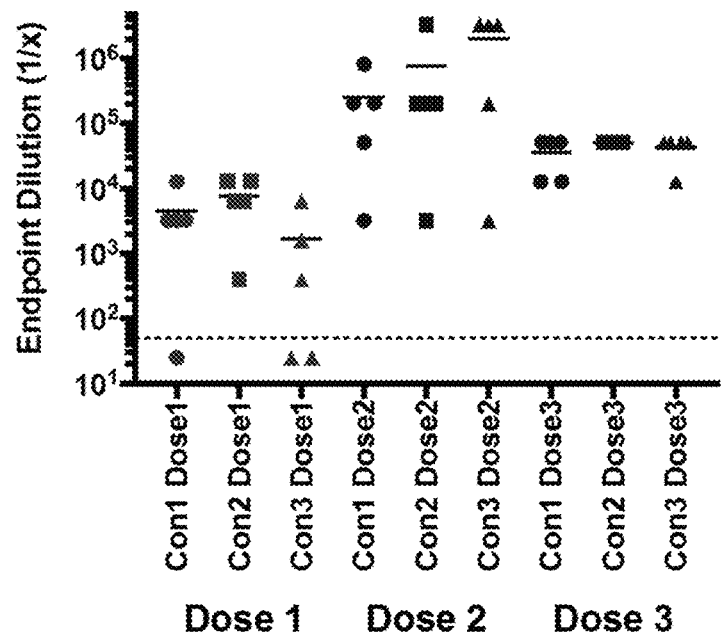
FIG. 6D depicts mouse anti-MARV GP IgG antibody endpoint titers as measured by ELISA binding to recombinant Angola GP protein (N=5 animals per group).
Figure 6E:
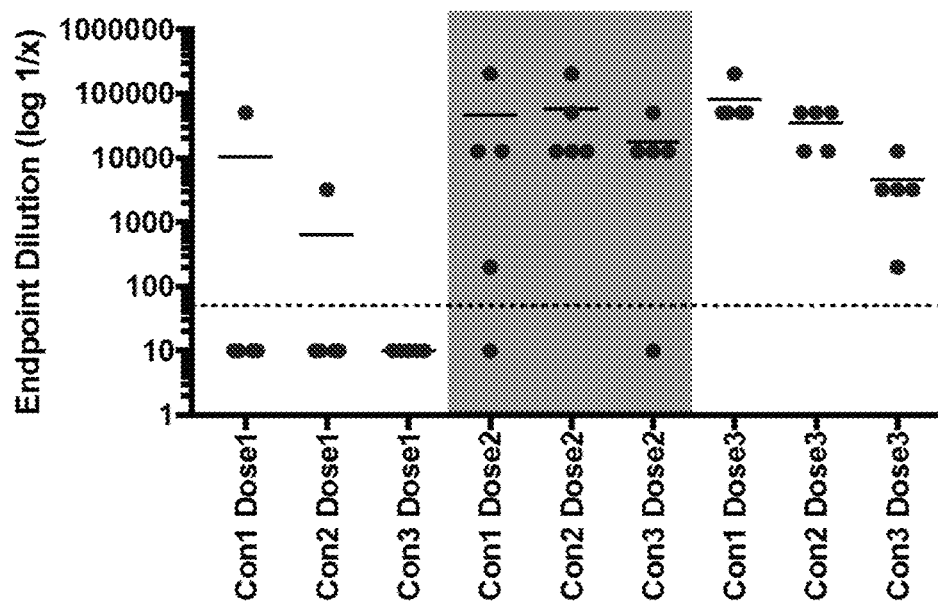
FIG. 6E depicts mouse anti-MARV GP IgG antibody endpoint titers as measured by ELISA binding to Musoke MARV virus-like-particles (N=5 animals per group).

Phylogenetic analysis revealed that the MARV GP (MGP) are divergent (~70% conserved). Thus, three different consensus MARV GP immunogens were developed (FIG. 2). Each GP transgene was genetically optimized, synthesized commercially, and then subcloned into a mammalian expression vector. HEK 293T cells were transfected separately with each plasmid and GP expression was assessed by Western immunoblotting (FIG. 3A) and FACS (FIG. 3B).

'Single-Dose' T-Cell Response in Mice

Figures 4A, 4B, 4C:
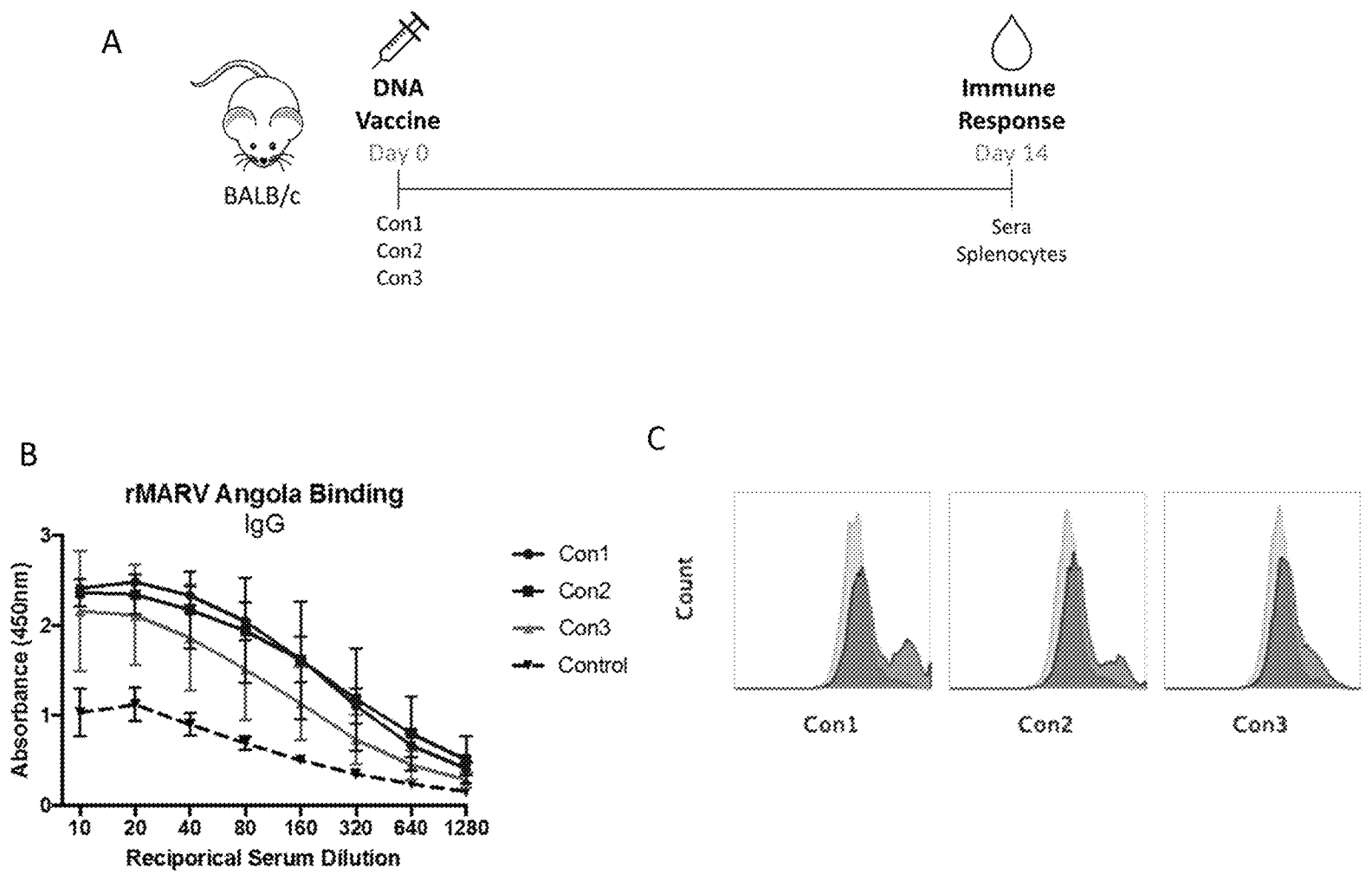

Vaccine response in mice was next assessed. BALB/c mice were immunized with 40 µg of plasmid DNA only once and sera splenocytes were evaluated 14 days after injection (FIG. 4A). Serum Abs were assessed and, as shown in FIG. 4B and FIG. 4C, increased levels of Ab binding was detected with all vaccines (Con1-Con3).

Figures 5A, 5B, 5C:
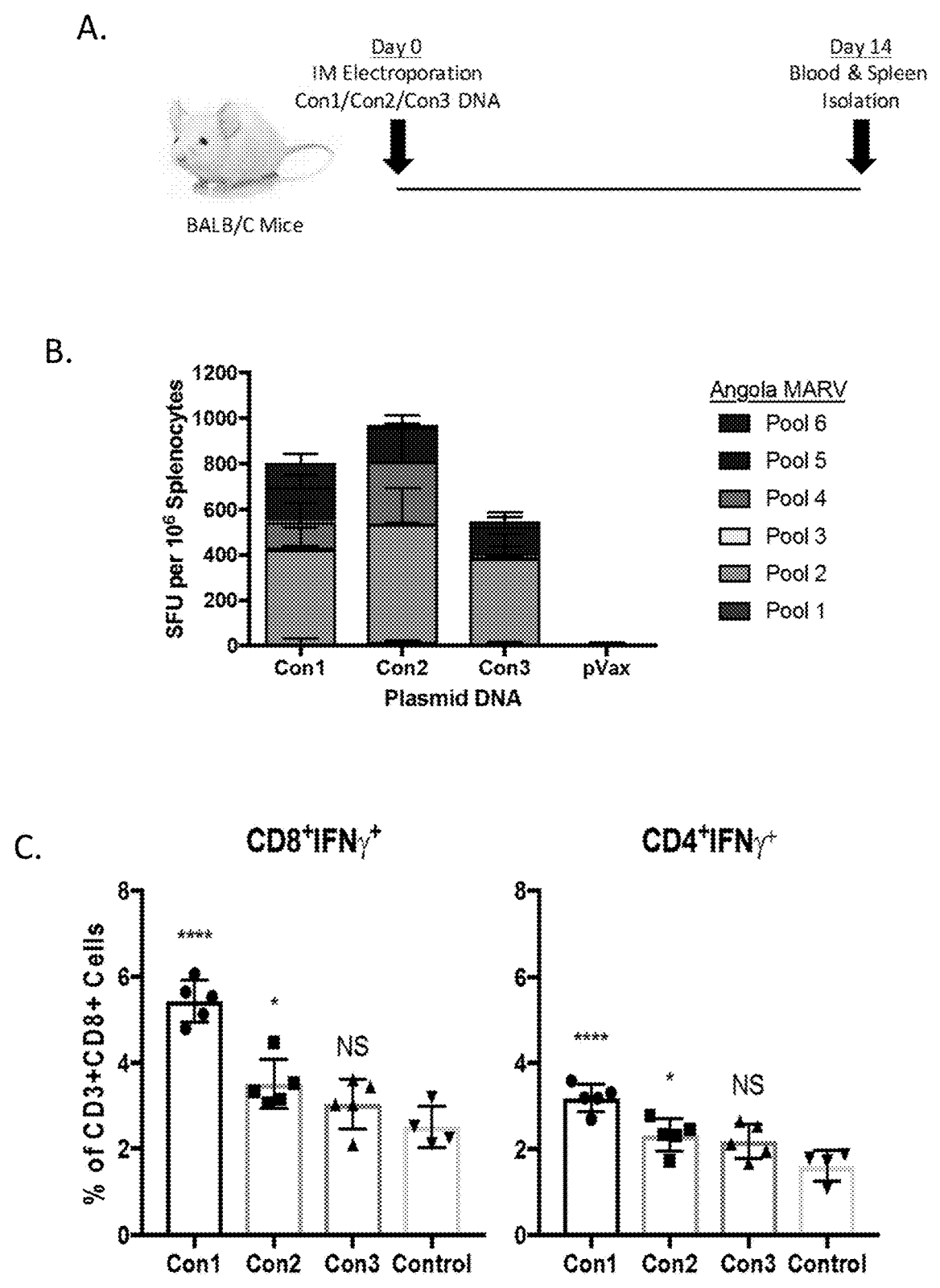

The generation of GP-specific T cells responses were then evaluated. FIGS. 5A and 5B show T cell induction by 'single-dose' vaccination. IFNγ-producing T cells were detected in all animals, and animals immunized with Con1 and Con2 has a significant increase in percentage of IFNγ-producing T cells over control cells.

It is demonstrated herein that consensus Marburg glycoprotein constructs are expressed in transfected cells. A single delivery of consensus Marburg glycoprotein constructs to mice generates anti-MARV antibodies and robust IFNγ T cell responses.

Figures 5D, 5E:
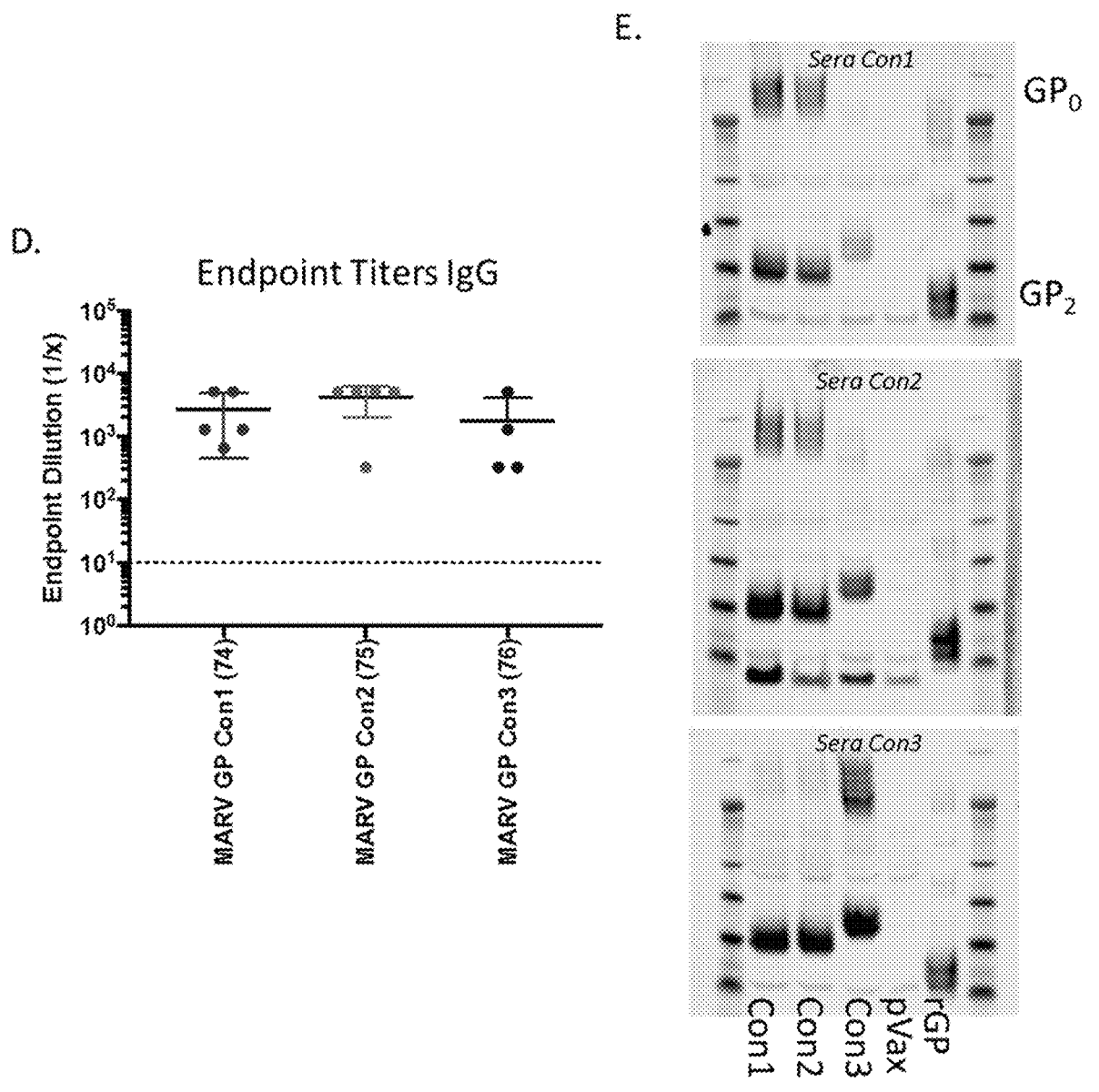
Figures 7D, 7E:
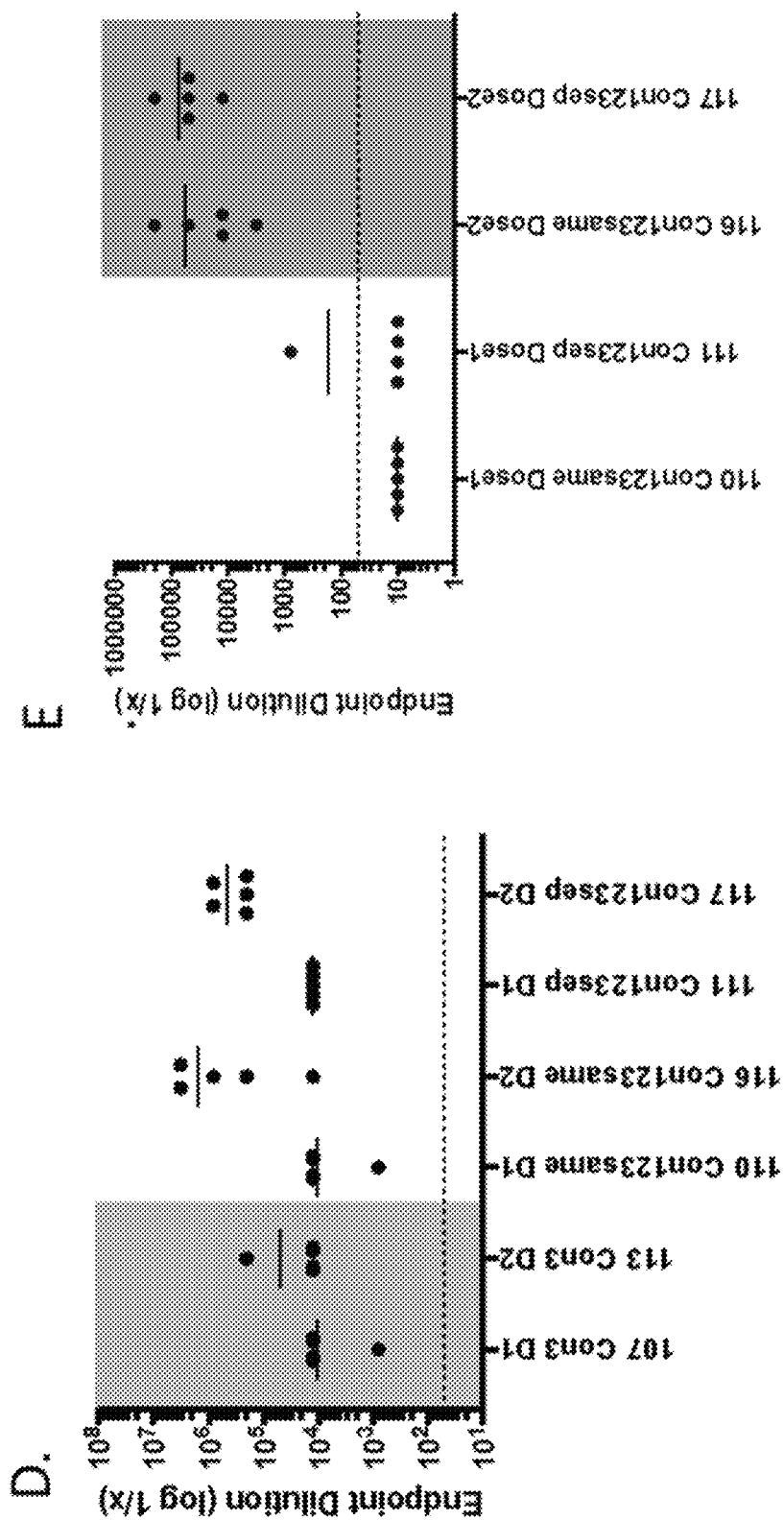
FIG. 7D depicts mouse anti-MARV GP IgG antibody endpoint titers as measured by ELISA binding to recombinant Angola GP protein (N=5 animals per group).
FIG. 7E depicts mouse anti-MARV GP IgG antibody endpoint titers as measured by ELISA binding to Musoke MARV virus-like-particles (N=5 animals per group).

FIG. 5 demonstrates that a single vaccination with the individual constructs induces T-Cell IFNγ response and antibody responses in mice. FIG. 6 and FIG. 7 demonstrate the breadth of T-Cell and antibody responses to MARV consensus vaccine constructs.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An immunogenic composition comprising a nucleic acid molecule, wherein the nucleic acid molecule encodes a peptide comprising an amino acid sequence selected from the group consisting of
   a) an amino acid sequence having at least about 90% identity over an entire length of the amino acid sequence selected from the group consisting of SEQ ID NO:2 and SEQ ID NO:4,
   b) an immunogenic fragment comprising at least about 90% identity over at least 60% of the amino acid sequence selected from the group consisting of SEQ ID NO:2 and SEQ ID NO:4,
   c) the amino acid sequence selected from the group consisting of SEQ ID NO:2, SEQ ID NO: 4 and SEQ ID NO:6, and
   d) an immunogenic fragment comprising at least 70% of the amino acid sequence selected from the group consisting of SEQ ID NO:2, SEQ ID NO:4 and SEQ ID NO:6.

2. The immunogenic composition of claim 1, wherein the nucleic acid molecule comprises a nucleotide sequence selected from the group consisting of
   a) a nucleotide sequence having at least about 90% identity over an entire length of a nucleotide sequence selected from the group consisting of SEQ ID NO:1, SEQ ID NO:3 and SEQ ID NO:5, b) an immunogenic fragment of a nucleotide sequence having at least about 60% of the nucleotide sequence selected from the group consisting of SEQ ID NO:1, SEQ ID NO:3 and SEQ ID NO:5, and c) a nucleotide sequence selected from the group consisting of SEQ ID NO:1, SEQ ID NO: 3 and SEQ ID NO:5.

3. The immunogenic composition of claim 1, wherein a nucleotide sequence encoding the peptide is operably linked to at least one regulatory sequence selected from the group consisting of a start codon, an IgE leader sequence and a stop codon.

4. The immunogenic composition of claim 3, wherein the nucleic acid molecule encodes a peptide comprising an amino acid sequence selected from the group consisting of
   a) an amino acid sequence having at least about 90% identity over an entire length of the amino acid sequence selected from the group consisting of SEQ ID NO:2 and SEQ ID NO:4,
   b) an immunogenic fragment comprising at least about 90% identity over at least 60% of the amino acid sequence selected from the group consisting of SEQ ID NO:2 and SEQ ID NO:4,
   c) the amino acid sequence selected from the group consisting of SEQ ID NO:2, SEQ ID NO: 4 and SEQ ID NO:6, and
   d) an immunogenic fragment comprising at least 70% of the amino acid sequence selected from the group consisting of SEQ ID NO:2, SEQ ID NO:4 and SEQ ID NO:6,
   operably linked to an amino acid sequence as set forth in SEQ ID NO:8.

5. The immunogenic composition of claim 4, wherein the nucleic acid molecule comprises a nucleotide sequence selected from the group consisting of
   a) a nucleotide sequence having at least about 90% identity over an entire length of a nucleotide sequence selected from the group consisting of SEQ ID NO:1, SEQ ID NO:3 and SEQ ID NO:5,
   b) an immunogenic fragment of a nucleotide sequence having at least about 60% of the nucleotide sequence selected from the group consisting of SEQ ID NO:1, SEQ ID NO:3 and SEQ ID NO:5, and
   c) a nucleotide sequence selected from the group consisting of SEQ ID NO:1, SEQ ID NO: 3 and SEQ ID NO:5
   operably linked to an nucleotide sequence encoding SEQ ID NO:8.

6. The immunogenic composition of claim 1, wherein the nucleic acid molecule comprises an expression vector.

7. The immunogenic composition of claim 1, further comprising a pharmaceutically acceptable excipient or an adjuvant.

8. A nucleic acid molecule encoding a peptide comprising an amino acid sequence selected from the group consisting of
   a) an amino acid sequence having at least about 90% identity over an entire length of the amino acid sequence selected from the group consisting of SEQ ID NO:2 and SEQ ID NO:4,
   b) an immunogenic fragment comprising at least about 90% identity over at least 60% of the amino acid sequence selected from the group consisting of SEQ ID NO:2 and SEQ ID NO:4,
   c) the amino acid sequence selected from the group consisting of SEQ ID NO:2, SEQ ID NO: 4 and SEQ ID NO:6, and
   d) an immunogenic fragment comprising at least 70% of the amino acid sequence selected from the group consisting of SEQ ID NO:2, SEQ ID NO:4 and SEQ ID NO:6.

9. The nucleic acid molecule of claim 8, wherein the nucleic acid molecule comprises a nucleotide sequence selected from the group consisting of
   a) a nucleotide sequence having at least about 90% identity over an entire length of a nucleotide sequence selected from the group consisting of SEQ ID NO:1, SEQ ID NO:3 and SEQ ID NO:5,
   b) an immunogenic fragment of a nucleotide sequence having at least about 60% of the nucleotide sequence selected from the group consisting of SEQ ID NO:1, SEQ ID NO:3 and SEQ ID NO:5, and
   c) a nucleotide sequence selected from the group consisting of SEQ ID NO:1, SEQ ID NO: 3 and SEQ ID NO:5.

10. The nucleic acid molecule of claim 8, wherein the encoded peptide is operably linked to at least one regulatory sequence selected from the group consisting of a start codon, an IgE leader sequence and a stop codon.

11. The nucleic acid molecule of claim 10, wherein the nucleic acid molecule encodes a peptide comprising an amino acid sequence selected from the group consisting of
   a) an amino acid sequence having at least about 90% identity over an entire length of the amino acid sequence selected from the group consisting of SEQ ID NO:2 and SEQ ID NO:4,
   b) an immunogenic fragment comprising at least about 90% identity over at least 60% of the amino acid sequence selected from the group consisting of SEQ ID NO:2 and SEQ ID NO:4,
   c) the amino acid sequence selected from the group consisting of SEQ ID NO:2, SEQ ID NO: 4 and SEQ ID NO:6, and
   d) an immunogenic fragment comprising at least 70% of the amino acid sequence selected from the group consisting of SEQ ID NO:2, SEQ ID NO:4 and SEQ ID NO:6,
   operably linked to an amino acid sequence as set forth in SEQ ID NO:8.

12. The nucleic acid molecule of claim 11, wherein the nucleic acid molecule comprises a nucleotide sequence selected from the group consisting of
   a) a nucleotide sequence having at least about 90% identity over an entire length of a nucleotide sequence selected from the group consisting of SEQ ID NO:1, SEQ ID NO:3 and SEQ ID NO:5,
   b) an immunogenic fragment of a nucleotide sequence having at least about 60% of the nucleotide sequence selected from the group consisting of SEQ ID NO:1, SEQ ID NO:3 and SEQ ID NO:5, and
   c) a nucleotide sequence selected from the group consisting of SEQ ID NO:1, SEQ ID NO: 3 and SEQ ID NO:5
   operably linked to an nucleotide sequence encoding SEQ ID NO:8.

13. The nucleic acid molecule of claim 8, wherein the nucleic acid molecule comprises an expression vector.

14. A peptide comprising an amino acid sequence selected from the group consisting of
   a) an amino acid sequence having at least about 90% identity over an entire length of the amino acid sequence selected from the group consisting of SEQ ID NO:2 and SEQ ID NO:4, b) an immunogenic fragment comprising at least about 90% identity over at least 60% of the amino acid sequence selected from the group consisting of SEQ ID NO:2 and SEQ ID NO:4,
c) the amino acid sequence selected from the group consisting of SEQ ID NO:2, SEQ ID NO: 4 and SEQ ID NO:6, and
d) an immunogenic fragment comprising at least 70% of the amino acid sequence selected from the group consisting of SEQ ID NO:2, SEQ ID NO:4 and SEQ ID NO:6.

15. A method of inducing an immune response against a Marburgvirus antigen in a subject in need thereof, the method comprising administering an immunogenic composition of claim 1 to the subject.

16. The method of claim 15, wherein administering includes at least one of electroporation and injection.

17. A method of treating or preventing a Marburgvirus associated pathology in subject in need thereof, the method comprising administering an immunogenic composition of claim 1 to the subject.

18. The method of claim 17, wherein administering includes at least one of electroporation and injection.

19. The method of claim 17, wherein the Marburgvirus associated pathology is at least one of Marburgvirus infection and hemorrhagic fever.

20. An immunogenic composition comprising a peptide of claim 14.

\* \* \* \* \*

SEQUENCE LISTING

```
Sequence total quantity: 8
SEQ ID NO: 1            moltype = DNA   length = 2040
FEATURE                 Location/Qualifiers
misc_feature            1..2040
                        note = Nucleotide sequence of Marburg marburgvirus
                         consensus envelope glycoprotein immunogen (Con1)
source                  1..2040
                        mol_type = other DNA
                        organism = synthetic construct
SEQUENCE: 1
aagaccacat gcctgttcat cagcctgatc ctgatccagg gcgtgaagac cctgccaatc   60
ctggagatcg cctccaacaa tcagccccag aacgtggaca gcgtgtgctc tggcaccctg  120
cagaagacga aggatgtgca cctgatgggc ttcacactga gcggacagaa ggtggcagac  180
tccccactgg aggcctctaa gaggtgggcc tttagaaccg gcgtgcccc taagaacgtg   240
gagtacaccg agggcgagga ggccaagaca tgctataata tctccgtgac cgatcccgac  300
ggcaagtccc tgctgctgga cccacccaca aacatcaggg attaccctaa gtgtaagacc  360
atccaccaca tccagggcca gaatccacac gcacagggaa tcgccctgca cctgtggggc  420
gccttctttc tgtacgacag gatcgccagc accacaatgt atagaggcaa ggtgttcaca  480
gagggcaaca tcgccgccat gatcgtgaat aagaccgtgc acaagatgat ctttctagg   540
cagggccagg gctacagaca catgaacctg acaagcacca ataagtattg gacaagctcc  600
aacggcacac agaccaatga caccggatgc ttcggcgccc tgcaggagta caactccacc  660
aagaatcaga catgtgcccc atctaagatc cctctgccac tgccaacagc aaggccagag  720
gtgaagctga catctaccag cacagacgcc accaagctga acaccacaga cccaattcc   780
gacgatgagg atctgaccac atccggctct ggcagcggag agcaggagcc ttataccaca  840
tctgatgccg ccaccaagca gggcctgtct agcaccatgc ctccaacacc tagcccacag  900
ccctccacac ctcagcagga gggcaacaat accaaccact ctcagggagc agtgaccgag  960
cctgccaaga caaacaccac agcccagcca agcatgcccc ctcacaatac cacagccatc 1020
agcaccaaca atacatccaa gcacaacttt tctaccccta gcgtgccact gcagaatgcc 1080
accaactaca atacacagtc caccgccaca gagaacgagc agacatccgc ccctctaag   1140
accacactgc cacccaccga gaaccctacc acagccaaga gcaccaattc cacaaagtct 1200
ccaaccacaa ccgtgcccaa cacaaccaat aagcactcca cctctcctag cccacccccc 1260
aaccctacag cccagcacct ggtgtatttc aggagaaagc ggaatatcct gtggcgcgga 1320
ggcgacatgt tccccttct ggatggcctg atcaacgccc ctatcgactt cgatccagtg   1380
cccaatacca agacaatctt tgacgagtgc tctagtccg gagcaagcgc cgaggaggat  1440
cagcacgcct ctcctaacat cagcctgaca ctgtcctact ttccaaagat caacgagaat 1500
accgcctatt ccggcgagaa cgagaatgac tgcgatgccg agctgaggat ctggagcgtg 1560
caggaggacg atctggcagc aggactgtcc tggattccct tcttcggacc tggaatcgag 1620
ggactgtaca ccgcaggact gatcaagaac cagaacaacc tggtgtgcag actgcggcgc 1680
ctggccaatc agacagccaa gtccctggag ctgctgctgc gggtgacaac cgaggagcgc 1740
accttctctc tgatcaaccg gcacgccatc gactttctgc tggcaagatg gggcggcacc 1800
tgcaaggtgc tgggaccaga ctgctgtatc ggcatcgagg atctgtctcg gaatatcagc 1860
gagcagatcg accagatcaa gaaggatgag cagaaggagg gaaccggatg gggactgggc 1920
ggcaagtggt ggacaagcga ttggggcgtg ctgaccaacc tgggcatcct gctgctgctg 1980
tctatcgccg tgctgatcgc cctgagctgc atctgtcgca tcttcaccaa gtatatcggc 2040

SEQ ID NO: 2            moltype = AA   length = 680
FEATURE                 Location/Qualifiers
REGION                  1..680
                        note = Amino acid sequence of Marburg marburgvirus
                         consensus envelope glycoprotein immunogen (Con1)
source                  1..680
                        mol_type = protein
                        organism = synthetic construct
SEQUENCE: 2
KTTCLFISLI LIQGVKTLPI LEIASNNQPQ NVDSVCSGTL QKTEDVHLMG FTLSGQKVAD   60
SPLEASKRWA FRTGVPPKNV EYTEGEEAKT CYNISVTDPS GKSLLLDPPT NIRDYPKCKT  120
IHHIQGQNPH AQGIALHLWG AFFLYDRIAS TTMYRGKVFT EGNIAAMIVN KTVHKMIFSR  180
QGQGYRHMNL TSTNKYWTSS NGTQTNDTGC FGALQEYNST KNQTCAPSKI PLPLPTARPE  240
VKLTSTSTDA TKLNTTDPNS DDEDLTTSGS GSGEQEPYTT SDAATKQGLS STMPPTSPQ   300
PSTPQQEGNN TNHSQGAVTE PGKTNTTAQP SMPPHNTTAI STNNTSKHNF STPSVPLQNA  360
TNYNTQSTAT ENEQTSAPSK TTLPPTENPT TAKSTNSTKS PTTTVPNTTN KHSTSPSPTP  420
NPTAQHLVYF RRKRNILWRE GDMFPFLDGL INAPIDFDPV PNTKTIFDES SSGASAEED   480
QHASPNISLT LSYFPKINEN TAYSGENEND CDAELRIWSV QEDDLAAGLS WIPFFGPGIE  540
GLYTAGLIKN QNNLVCRLRR LANQTAKSLE LLLRVTTEER TFSLINRHAI DFLLARWGGT  600
CKVLGPDCCI GIEDLSRNIS EQIDQIKKDE QKEGTGWGLG GKWWTSDWGV LTNLGILLLL  660
SIAVLIALSC ICRIFTKYIG                                             680

SEQ ID NO: 3            moltype = DNA   length = 2040
FEATURE                 Location/Qualifiers
misc_feature            1..2040
                        note = Nucleotide sequence of Marburg marburgvirus
                         consensus envelope glycoprotein immunogen (Con2)
source                  1..2040
                        mol_type = other DNA
                        organism = synthetic construct
SEQUENCE: 3
aagaccacat gcctgttcat cagcctgatc ctgatccagg gcgtgaagac cctgccaatc   60
ctggagatcg cctccaacaa tcagccccag aacgtggaca gcgtgtgctc tggcaccctg  120
```

```
cagaagacag aggatgtgca cctgatgggc ttcacactga gcggacagaa ggtggcagac  180
tccccactgg aggcctctaa gaggtgggcc tttagaaccg gcgtgcccc  taagaacgtg  240
gagtacaccg agggcgagga ggccaagaca tgctataata tctccgtgac cgatcccagc  300
ggcaagtccc tgctgctgga cccacccaca aacatcaggg attaccctaa gtgtaagacc  360
atccacacca tccagggcca gaatccacac gcacaggaca tcgccctgca cctgtggggc  420
gccttctttc tgtacgacag gatcgccagc accacaatgt atagaggcaa ggtgttcaca  480
gagggcaaca tcgccgccat gatcgtgaat aagaccgtgc acaagatgat cttttctagg  540
cagggccagg gctacagaca catgaacctg acaagcacca ataagtattg gacaagctcc  600
aacggcacac agaccaatga cacccggatgc ttcggcgccc tgcaggagta caactccacc  660
aagaatcaga catgtgcccc atctaagatc cctctgccac tgccaacagc aaggccagag  720
gtgaagctga catctaccag cacagacgcc accaagctga acaccacaga ccccaattcc  780
gacgatgagg atctgaccac atccggctct ggcagcggag agcaggagcc ttataccaca  840
tctgatgccg ccaccaagca gggcctgtct agcaccatgc ctccaacacc tagcccacag  900
ccctccacac ctcagcagga gggcaacaat accaaccact ctcagggagc agtgaccgag  960
cctggcaaga caaacaccac agcccagcca agcatgcccc tcacaatac acagccatc  1020
agcaccaaca atacatccaa gcacaacttt ctcacccta gcgtgccact gcagaatgcc  1080
accaactaca atacacagtc caccgccaca gagaacgagc agacatccgc ccctctaag  1140
accacactgc cacccaccga gaaccctacc acagccaaga caccaattc cacaaagtct  1200
ccaaccacaa ccgtgcccaa cacaaccaat aagcactcca cctctcctag cccaaccccc  1260
aaccctacag cccagcacct ggtgtatttc aggagaaagc ggaatatcct gtggcgcgag  1320
ggcgacatgt tccccttttct ggatggcctg atcaacgccc tatcgactt cgatccagtg  1380
cccaatacca agacaatctt tgacgatcc tctagctccg gcagcagcgg cgaggaggat  1440
cagcacgcct ctcctaacat cagcctgaca ctgtcctact ttccaaagat caacgagaat  1500
accgccatt ccggcgagaa cgagaatgac tgcgatgccg agctgaggat ctggagcgtg  1560
caggaggacg atctggcagc aggactgtcc tggattcct tcttcggacc tggaatcgag  1620
ggactgtaca ccgcaggact gatcaagaac cagaacaagc tgtgtgcag actgcggcgt  1680
ctggccaatc agacagccaa gtccctggag ctgctgctgc gggtgacaac cgaggagcgc  1740
acccttctctc tgatcaaccg gcacgccatc gactttctgc tggcaagatg gggcggcacc  1800
tgcaaggtgc tgggacagga ctgctgtatc ggcatcgagg atctgtctcg aatatcagc  1860
gagcgaatcg accagatcaa gaaggatgag cagaaggagg aaccggatg gggactggc  1920
ggcaagtggt ggacaagcga ttggggcgtg ctgaccaacc tgggcatcct gctgctgctg  1980
tctatcgccg tgctgatcgc cctgagctgc atctgtcgca tcttcaccaa gtatatcggc  2040
```

```
SEQ ID NO: 4              moltype = AA  length = 680
FEATURE                   Location/Qualifiers
REGION                    1..680
                          note = Amino acid sequence of Marburg marburgvirus
                           consensus envelope glycoprotein immunogen (Con2)
source                    1..680
                          mol_type = protein
                          organism = synthetic construct
SEQUENCE: 4
RTTCFFISLI LIQGIKTLPI LEIASNDQPQ NVDSVCSGTL QKTEDVHLMG FTLSGQKVAD   60
SPLEASKRWA FRTGVPPKNV EYTEGEEAKT CYNISVTDPS GKSLLLDPPT NVRDYPKCKT  120
IHHIQGQNPH AQGIALHLWG AFFLYDRIAS TTMYRGKVFT EGNIAAMIVN KTVHKMIFSR  180
QGQGYRHMNL TSTNKYWTSS NGTQTNDTGC FGTLQEYNST KNQTCAPSKT PPPPPTARPE  240
IKPTSTPTDA TRLNTTNPNS DDEDLTTSGS GSGEQEPYTT SDAVTKQGLS STMPPTPSPQ  300
PGTPQQGGNN TNHSQDATTE LDNTNTTAQP PMPSHNTTTI STNNTSKHNL STLSEPPQNT  360
TNPNTQSMVT ENEKTSAPPK ATLPPTENPT TEKSTNNTKS PTTLEPNKTN GHFTSPSSTP  420
NSTTQHLIYF RRKRSILWRE GDMFPFLDGL INAPIDFDPV PNTKTIFDES SSSGASAEED  480
QHASSNISLT LSYLPHTSEN TAYSGENEND CDAELRIWSV QEDDLAAGLS WIPLFGPGIE  540
GLYTAGLIKN QNNLVCRLRR LANQTAKSLE LLLRVTTEER TFSLINRHAI DFLLTRWGGT  600
CKVLGPDCCI GIEDLSRNIS EQIDQIKKDE QKEGTGWGLG GKWWTSDWGV LTNLGILLLL  660
SIAVLIALSC ICRIFTKYIG                                              680

SEQ ID NO: 5              moltype = DNA  length = 2040
FEATURE                   Location/Qualifiers
misc_feature              1..2040
                          note = Nucleotide sequence of Marburg marburgvirus
                           consensus envelope glycoprotein immunogen (Con 3)
source                    1..2040
                          mol_type = other DNA
                          organism = synthetic construct
SEQUENCE: 5
aagacaatct acttcctgat ctctctgatc ctgatccaga gcatcaagac cctgccagtg   60
ctggagatcg cctccaactc tcagcccag gacgtggata gcgtgtgctc tggcaccctg  120
cagaagacag aggacgtgca cctgatgggc ttcacactgt ccggcagaa ggtggccgat  180
tccccctctg aggcctctaa gaggtgggcc tttagaaccg gcgtgcccc  taagaacgtg  240
gagtacaccg agggcgagga ggccaagaca tgctataata tctccgtgac cgacccaagc  300
ggcaagtccc tgctgctgga cccacccctc aacatcaggg attaccccaa gtgtaagacc  360
gtgcaccaca tccagggcca gaatcctcac gcacagggaa tcgccctgca cctgtggggc  420
gccttctttc tgtacgatcg ggtggccagc accacaatgt atcgcggcaa ggtgttcaca  480
gagggcaaca tcgccgccat gatcgtgaat aagaccgtgc accggatgat cttttctcgc  540
cagggccagg gctacaggca catgaacctg accagcacca ataagtattg gacaagctcc  600
aacgagaccc agaaaatga cacaggctgc tttggcatcc tgcaggagta taactccacc  660
aacaatcaga catgtcctcc aagcctgaag ccccttccc tgcctaccgt gacaccatct  720
atccacagca ccaacacaca gatcaatacc gccaagagcg gcaatgaa cccttctagc  780
gacgatgagg acctgatgat cagcggctcc ggctctggag agcagggacc acacaccaca  840
ctgaatgtgt tgaccgagca gaagcagtcc tctaccatcc tgtccacacc atctctgcac  900
```

```
ctgagcacat cccagcacga gcagaactct accaatccca gccggcacgc agtgaccgag    960
cacaacggca cagaccccac cacacagcct gccaccctgc tgaacaatac aaataccaca   1020
cctacctaca acacactgaa gtataatctg agcacaccat ccccacccac caggaacatc   1080
acaaacaatg atacccagag agagctggcc gagtccgagc agaccaacgc ccagctgaat   1140
accacactgg acccaacaga gaaccccacc acaggccagg ataccaactc taccacaaat   1200
atcatcatga ccacatccga catcacctct aagcacccaa caaatagctc ccctgattct   1260
agcccaacca cacgccctcc aatctacttc aggaagaaga ggagcatctt ttggaaggag   1320
ggcgacatct tcccctttct ggatggcctg atcagcaccg agatcgactt cgatccaatc   1380
cccaacaccg agacaatctt cgacgagtct cccagcttta acacctccac aaatgaggag   1440
cagcacacac ccctaacat cagcctgacc ttctcctact ttcctgacaa gaatggcgat   1500
accgcctata gcggcgagaa cgagaatgac tgcgatgccg agctgcggat ctggagcgtg   1560
caggaggacg atctggcagc aggactgcc tggattccct tcttcggccc tggcatcgag   1620
ggcctgtata ccgccggcct gatcaagaac cagaacaacc tggtgtgccg cctgaggaga   1680
ctggccaatc agacagccaa gagcctggag ctgctgctga ggtgaccac agaggagaga   1740
accttctccc tgatcaaccg gcacgccatc gactttctgc tgacccgctg gggcggcaca   1800
tgcaaggtgc tgggaccaga ctgctgtatc ggcatcgagg atctgtctaa gaatatcagc   1860
gagcagatcg acaagatcag gaaggatgag cagaaggagg agaccggatg gggactgggc   1920
ggcaagtggt ggacaagcga ttggggcgtg ctgaccaacc tgggcatcct gctgctgctg   1980
tccatcgccg tgctgatcgc cctgtcttgc atctgtagaa tcttcaccaa gtacatcggc   2040

SEQ ID NO: 6             moltype = AA  length = 680
FEATURE                  Location/Qualifiers
REGION                   1..680
                         note = Amino acid sequence of Marburg marburgvirus
                         consensus envelope glycoprotein immunogen (Con 3)
source                   1..680
                         mol_type = protein
                         organism = synthetic construct
SEQUENCE: 6
KTIYFLISLI LIQSIKTLPV LEIASNSQPQ DVDSVCSGTL QKTEDVHLMG FTLSGQKVAD    60
SPLEASKRWA FRTGVPPKNV EYTEGEEAKT CYNISVTDPS GKSLLLDPPS NIRDYPKCKT   120
VHHIQGQNPH AQGIALHLWG AFFLYDRVAS TTMYRGKVFT EGNIAAMIVN KTVHRMIFSR   180
QGQGYRHMNL TSTNKYWTSS NETQRNDTGC FGILQEYNST NNQTCPPSLK PPSLPTVTPS   240
IHSTNTQINT AKSGTMNPSS DDEDLMISGS GSGEQGPHTT LNVVTEQKQS STILSTPSLH   300
LSTSQHEQNS TNPSRHAVTE HNGTDPTTQP ATLLNNTNTT PTYNTLKYNL STPSPPTRNI   360
TNNDTQRELA ESEQTNAQLN TTLDPTENPT TGQDTNSTTN IIMTTSDITS KHPTNSSPDS   420
SPTTRPPIYF RKKRSIFWKE GDIFPFLDGL ISTEIDFDPI PNTETIFDES PSFNTSTNEE   480
QHTPPNISLT FSYFPDKNGD TAYSGENEND CDAELRIWSV QEDDLAAGLS WIPFFGPGIE   540
GLYTAGLIKN QNNLVCRLRR LANQTAKSLE LLLRVTTEER TFSLINRHAI DFLLTRWGGT   600
CKVLGPDCCI GIEDLSKNIS EQIDKIRKDE QKEETGWGLG GKWWTSDWGV LTNLGILLLL   660
SIAVLIALSC ICRIFTKYIG                                               680

SEQ ID NO: 7             moltype = DNA  length = 54
FEATURE                  Location/Qualifiers
misc_feature             1..54
                         note = Nucleotide sequence encoding an IgE signal peptide
source                   1..54
                         mol_type = other DNA
                         organism = synthetic construct
SEQUENCE: 7
atggactgga cctggatcct gttcctggtg gccgctgcca cacgggtgca cagc           54

SEQ ID NO: 8             moltype = AA  length = 18
FEATURE                  Location/Qualifiers
REGION                   1..18
                         note = Amino acid sequence for the IgE signal peptide
source                   1..18
                         mol_type = protein
                         organism = synthetic construct
SEQUENCE: 8
MDWTWILFLV AAATRVHS                                                   18
```